US009168389B2

(12) United States Patent
Langer et al.

(10) Patent No.: US 9,168,389 B2
(45) Date of Patent: Oct. 27, 2015

(54) HARMONIC GENERATION FOR ACTIVATION OF SPECIES AND/OR DELIVERY OF SPECIES TO A TARGET ENVIRONMENT

(71) Applicants: Massachusetts Institute of Technology, Cambridge, MA (US); Children's Medical Center Corporation, Boston, MA (US)

(72) Inventors: Robert S. Langer, Newton, MA (US); Daniel S. Kohane, Newton, MA (US); Aoune Barhoumi, Boston, MA (US)

(73) Assignees: Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 106 days.

(21) Appl. No.: 13/771,565

(22) Filed: Feb. 20, 2013

(65) Prior Publication Data

US 2014/0234938 A1    Aug. 21, 2014

(51) Int. Cl.
*C12N 13/00*     (2006.01)
*A61N 5/06*      (2006.01)

(52) U.S. Cl.
CPC ..................................... *A61N 5/062* (2013.01)

(58) Field of Classification Search
None
See application file for complete search history.

(56) References Cited

U.S. PATENT DOCUMENTS 6,123,923 A * 9/2000 Unger et al. ................. 424/9.52

OTHER PUBLICATIONS

Dvir et al., "Photo-targeted nanoparticles." *Nano Lett.* Jan. 2010; 10(1): 250-4.
Kim et al., "High-harmonic generation by resonant plasmon field enhancement." *Nature.* Jun. 5, 2008; 453(7196): 757-60.
Timko et al., "Remotely triggerable drug delivery systems." *Adv Mater.* Nov. 24, 2010; 22(44): 4925-43.
Tong et al., "Shedding light on nanomedicine." *Wiley Interdiscip Rev Nanomed Nanobiotechnol.* Nov.-Dec. 2012;4(6):638-62. Published online Aug. 9, 2012.

* cited by examiner

*Primary Examiner* — Hasan Ahmed
(74) *Attorney, Agent, or Firm* — Wolf, Greenfield & Sacks, P.C.

(57) ABSTRACT

Systems and methods for the activation of species and/or the delivery of species to a target environment using harmonic generation materials are generally described.

20 Claims, 13 Drawing Sheets

HARMONIC GENERATION FOR ACTIVATION OF SPECIES AND/OR DELIVERY OF SPECIES TO A TARGET ENVIRONMENT

TECHNICAL FIELD

Systems and methods for the activation of species and/or the delivery of species to a target environment using harmonic generation materials are generally described.

BACKGROUND

The ability to deliver compositions to targeted environments and/or to selectively activate compositions within specific spatial regions is important in a variety of fields. For example, targeted drug delivery strategies can be employed to deliver pharmaceutical compositions to a subject in a manner that increases the concentration of the pharmaceutical composition in some parts of the body relative to others, which can allow one to prolong drug interaction with specific diseased tissues. The ability to deliver pharmaceutical compositions to specific tissues can reduce dosage frequency, reduce unwanted side-effects caused by interactions of the pharmaceutical with non-targeted tissues, and reduce the fluctuation in the amount of the pharmaceutical composition circulating in the blood stream. Similar strategies can be employed in imaging applications, where it might be desirable to produce images of certain targeted locations.

Many targeted activation and/or release mechanisms are triggered using ultraviolet or higher-frequency electromagnetic radiation. Often, such electromagnetic radiation is transported through tissue to trigger activation and/or release. High-frequency electromagnetic radiation can cause unwanted side-effects, including tissue damage. For example, high-frequency electromagnetic radiation can cause photothermal damage, in which tissues are heated by absorbed electromagnetic radiation, which can in turn cause denaturation of proteins, loss of molecular tertiary structure, and fluidization of membranes. Electromagnetic radiation can also cause photochemical injury, for example, by generating free radicals. High-energy electromagnetic radiation can cause photomechanical damage, applying compressive or tensile forces to tissues.

Accordingly, it would be desirable to limit the extent to which high-frequency electromagnetic radiation interacts with the tissue of a subject in targeted release and/or activation systems.

SUMMARY

The use of harmonic generation materials for the activation of species and/or the delivery of species to a target environment, and associated systems and articles, are generally provided. In one set of embodiments, collagen is employed as a harmonic generation material in the delivery of an agent (e.g., pharmaceutical and/or imaging agents) to a target environment and/or in the activation of an agent, for example, within the body of a subject. The subject matter of the present invention involves, in some cases, interrelated products, alternative solutions to a particular problem, and/or a plurality of different uses of one or more systems and/or articles.

In one aspect, a method is provided. The method comprises, in certain embodiments, exposing, to a harmonic generation material, electromagnetic radiation of a first frequency and allowing the harmonic generation material to release electromagnetic radiation of a second, higher frequency; and exposing, to the electromagnetic radiation of the second frequency, a material photosensitive to the electromagnetic radiation of the second frequency such that when the photosensitive material absorbs the electromagnetic radiation of the second frequency, the photosensitive material is physically and/or chemically altered.

In one aspect, a system is provided. The system comprises, in certain embodiments, a harmonic generation material configured to convert at least a portion of electromagnetic radiation of a first frequency incident on the harmonic generation material to electromagnetic radiation of a second, higher frequency; a source configured to emit electromagnetic radiation of the first frequency such that the electromagnetic radiation of the first frequency is incident upon the harmonic generation material; and a photosensitive material configured to absorb the electromagnetic radiation of the second, higher frequency emitted by the harmonic generation material. In certain embodiments, the photosensitive material is configured such that, when the photosensitive material absorbs the electromagnetic radiation of the second frequency, the photosensitive material is physically and/or chemically altered.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
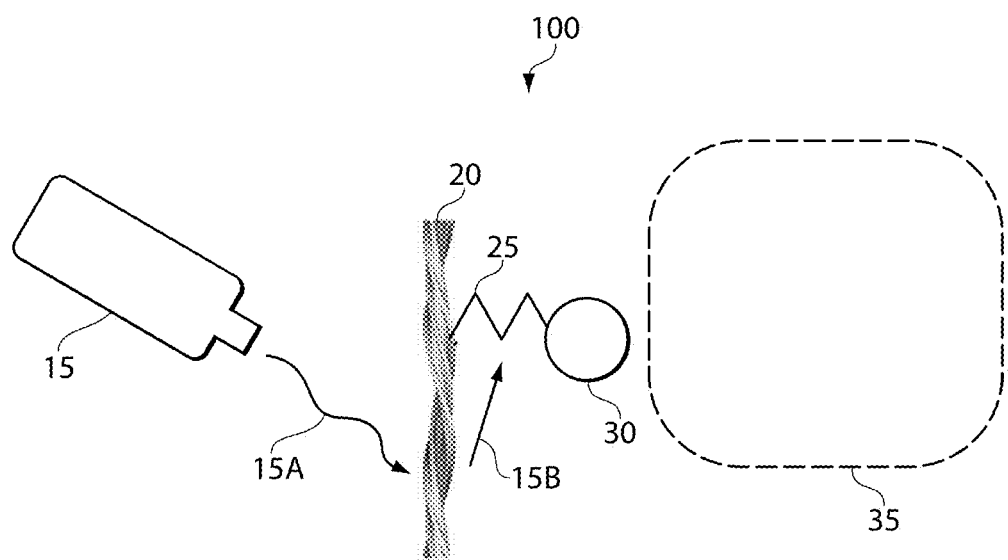
FIGS. 1A-1B are, according to certain embodiments, schematic illustrations of a system in which electromagnetic radiation emitted from a harmonic generation material is absorbed by a photosensitive material binding an agent to a harmonic generation material.

The use of harmonic generation to generate high-energy electromagnetic radiation that is subsequently used as a trigger (e.g., to activate species and/or to deliver species to a target environment) is generally described. In certain embodiments, harmonic generation material, such as collagen, can be used to convert incoming low-energy electromagnetic radiation to higher-energy electromagnetic radiation, which can be used to physically or chemically alter a photosensitive material. In some such embodiments, alteration of the photosensitive material can lead to the release or activation of an agent, such as a pharmaceutically active composition.

Harmonic generation is a nonlinear optical process in which a plurality of photons with the same energy are combined to form a photon with a higher amount of energy. For example, second harmonic generation occurs when two photons with the same energy combine to form a single photon with twice the energy (i.e., one-half of the wavelength and twice the frequency) of the original photons. While second harmonic generation is primarily described herein, the use of higher order harmonic generation processes (e.g., third harmonic generation, fourth harmonic generation, etc.) can also be used in addition to or in place of the second harmonic generation processes described herein.

Harmonic generation should not be confused with other frequency-multiplying phenomenon such as photon upconversion and two-photon absorption. Photon upconversion is a process by which the sequential absorption of two or more photons at a first wavelength leads to the emission of light at a second, shorter wavelength. Materials in which photon upconversion can take place generally contain ions of d-block and f-block elements, such as $Ti^{2+}$, $Ni^{2+}$, $Mo^{3+}$, $Re^{4+}$, and $Os^{4+}$. Two-photon absorption refers to the simultaneous absorption of two photons of identical or different frequencies in order to excite a molecule from one state to a higher energy electronic state; when the molecule relaxes to the lower-energy state, a single photon of higher energy than the initially-absorbed photons can be emitted.

Harmonic generation-based triggering systems can be particularly beneficial when it is undesirable to transmit electromagnetic radiation of the triggering wavelength over long distances. In certain inventive harmonic generation-based systems described herein, relatively low-energy electromagnetic radiation (e.g., infrared electromagnetic radiation) can be directed toward a harmonic generating material (e.g., collagen), and, upon interacting with the harmonic generating material, the low-energy electromagnetic radiation can be converted to high-energy electromagnetic radiation. The high-energy electromagnetic radiation generated by the harmonic generating material can subsequently be used to trigger an event, such as the activation of an agent and/or the delivery of an agent to a target region. Such an arrangement can allow for the transport of the low-energy electromagnetic radiation over a relatively long distance (thus avoiding the transmittance of high-energy electromagnetic radiation over a long distance) while maintaining the ability to deliver high-energy electromagnetic radiation to a target site.

The ability to produce high-energy electromagnetic radiation at targeted sites without transporting the high-energy radiation over long distances can be advantageous in a variety of applications. As one particular example, ultraviolet electromagnetic radiation is often used to trigger the release of drugs in targeted drug delivery systems. However, ultraviolet electromagnetic radiation can cause tissue damage and produce other undesirable side effects. In addition, it is often difficult to efficiently transmit ultraviolet radiation through tissue over long distances. Using the inventive systems and methods described herein, one can transmit relatively low-energy infrared radiation through the tissue and irradiate harmonic generating material to produce high-energy ultraviolet radiation only within targeted regions, thereby increasing radiation delivery efficiency and limiting tissue damage and other side effects.

Certain inventive aspects are related to the discovery that collagen can be effectively used as a harmonic generation material to produce targeted emissions of high-energy electromagnetic radiation for species activation and/or delivery. Collagen is the most abundant protein in mammals, and therefore is quite useful as a harmonic generation material as it is readily accessible within mammalian subjects. While collagen has been used as a second harmonic generating material for imaging applications, it is believed that electromagnetic radiation produced by harmonic generation materials such as collagen has not yet been employed to physically or chemically alter a photosensitive material (which can be used, for example, to trigger the release or activation of a species).

In some embodiments, a harmonic generation material may be exposed to electromagnetic radiation at a first frequency. The electromagnetic radiation may undergo one or more harmonic generation processes in the harmonic generation material, such that the electromagnetic radiation is released by the harmonic generation material at a second frequency. In certain embodiments, the second frequency may be higher than the first frequency. For example, the harmonic generation material may convert infrared or near infrared electromagnetic radiation (e.g., electromagnetic radiation having at least one frequency from about 700 nm to about 1,000 nm or from about 850 nm to about 2,500 nm, respectively) to ultraviolet electromagnetic radiation (e.g., electromagnetic radiation having at least one frequency from about 10 nm to about 380 nm).

In some embodiments, the harmonic generation material may be associated with a photosensitive material. In certain embodiments, the photosensitive material is exposed to the electromagnetic radiation of the second frequency. In some embodiments, the photosensitive material may be photosensitive to the electromagnetic radiation of the second frequency, for example, such that when the photosensitive material absorbs the electromagnetic radiation of the second frequency, the photosensitive material is physically and/or chemically altered. For example, absorption of the electromagnetic radiation at the second frequency may result in the breaking of one or more chemical bonds and/or an alteration in the molecular conformation of the photosensitive material. In certain embodiments, absorption of the electromagnetic radiation at the second frequency may result in the photosensitive material changing phases.

In certain embodiments, the harmonic generation material may be in close proximity to the photosensitive material. For example, in some embodiments, the closest distance between the harmonic generation material and the photosensitive material may be less than about 1 centimeter, less than about 1 millimeter, less than about 100 micrometers, less than about 10 micrometers, or less than about 1 micrometer. In some embodiments, the harmonic generation material and the photosensitive material may be in direct contact (e.g., they may be chemically bound to each other or otherwise in direct contact with each other). Positioning the harmonic generation material such that it is close to the photosensitive material can, in certain embodiments, ensure that a relatively high percentage of the electromagnetic radiation of the second, higher frequency generated by the harmonic generation material is able to reach and be absorbed by the photosensitive material.

In certain embodiments, the photosensitive material may be associated with an agent. Examples of agents include, but are not limited to, active pharmaceutical ingredients and imaging agents (e.g., luminescent materials, quantum dots, and the like). In certain embodiments, the photosensitive material may be bound to the agent, for example, via a covalent bond or an ionic bond. In certain embodiments, the photosensitive material and the agent may be associated with each other via electrostatic forces, van der Waals forces, or other such forces. In some embodiments, the agent may be at least partially surrounded by (and, in certain embodiments, substantially completely surrounded by) the photosensitive material, in the presence or absence of bonds and/or attractive forces between the photosensitive material and the agent. For example, in some embodiments, the agent can be contained within a shell, within a micelle, or within a liposome.

In some instances, the change in the photosensitive material induced by the electromagnetic radiation from the harmonic generation material may act to alter the agent (e.g., by activating the agent) or alter the interaction between the agent and the photosensitive material (e.g., via breaking a bond or changing the molecular conformation of the photosensitive material). The alteration of the agent and/or the interaction between the agent and the photosensitive material can lead to the activation of the agent (e.g., the activation of an active pharmaceutical ingredient) and/or to the delivery of the agent, for example, to a target region. Systems and methods of the present invention may be employed in applications involving triggered activation and/or release of one or more agents, though other applications are also possible.

The embodiments described herein are not limited to systems in which agents are employed, however. In certain embodiments, for example, delivery and/or activation of the photosensitive material itself may be desirable, and may be achieved using electromagnetic radiation emitted by the harmonic generation material. For example, the photosensitive material itself may be, in certain embodiments, pharmaceutically active.

In certain embodiments, when the photosensitive material absorbs the electromagnetic radiation of the second frequency emitted by the harmonic generation material, at least one chemical bond of the photosensitive material is broken. The chemical bond that is broken may be, for example, a covalent bond. In some embodiments, the chemical bond that is broken is a non-covalent bond, such as a hydrogen bond, ionic bond, dative bond, and/or a Van der Waals interaction.

Figure 1B:
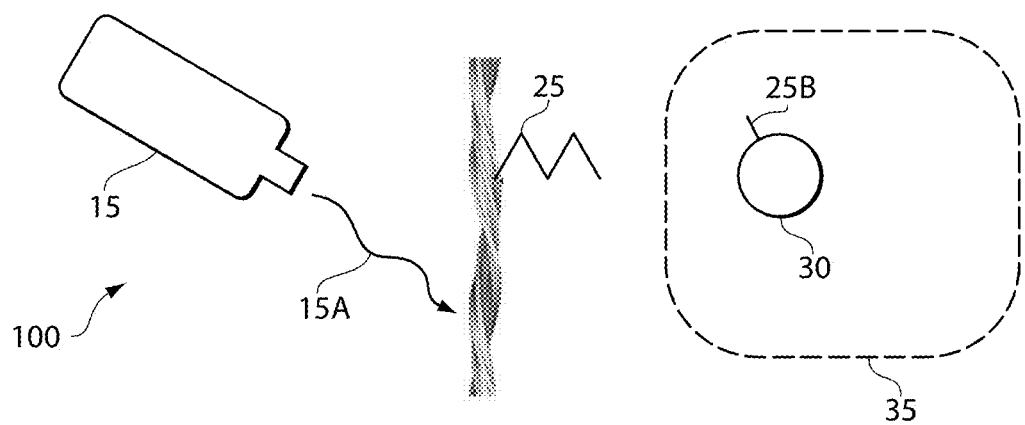

FIGS. 1A-1B are schematic diagrams of a system in which at least one chemical bond of a photosensitive material is broken after the photosensitive material absorbs electromagnetic radiation generated by a harmonic generation material. As shown in FIG. 1A, harmonic generation-based triggering system 100 may include harmonic generation material 20 and photosensitive material 25. System 100 may also include electromagnetic radiation source 15. In some embodiments, electromagnetic radiation source 15 may be directed toward the harmonic generation material 20 to expose the harmonic generation material to electromagnetic radiation at a first frequency 15A, as illustrated in FIGS. 1A-1B. The harmonic generation material 20 may convert at least a portion of the electromagnetic radiation having a first frequency 15A to electromagnetic radiation having a second frequency 15B. In certain embodiments, as illustrated in FIG. 1A, electromagnetic radiation 15B having the second frequency can be absorbed by photosensitive material 25. This can be accomplished, for example, by binding or otherwise contacting the photosensitive material to/with the harmonic generation material, as illustrated in FIGS. 1A-1B, or by positioning the harmonic generation material and the photosensitive material such that they are relatively close together.

In some embodiments, the photosensitive material may be associated with an agent. In some such embodiments, the agent and the photosensitive material may be in direct contact (e.g., bonded to each other or otherwise in direct contact). In other such embodiments, the photosensitive material and the agent may be proximate to each other, but not in direct contact with each other. For example, in some embodiments, the closest distance between the photosensitive material and the agent may be less than about 1 centimeter, less than about 1 millimeter, less than about 100 micrometers, less than about 10 micrometers, or less than about 1 micrometer.

As one particular example, referring back to FIG. 1A, the photosensitive material may function as a connector between the harmonic generation material and the agent. In some such embodiments, the photosensitive material may restrict the mobility and/or spatial orientation of the agent. In some instances, the photosensitive material may be a photosensitive bond or linker molecule (e.g., a bond or molecule that connects two or more structures) that connects the harmonic generation material and the agent.

In some embodiments, the electromagnetic radiation at the first frequency 15A may not affect the photosensitive material (e.g., may not break a bond of the photosensitive material, change the conformation of the photosensitive material, or otherwise substantially alter the photosensitive material).

However, the electromagnetic radiation at the second frequency 15B may cause a change in the photosensitive material (e.g., by breaking a bond, changing the molecular configuration, or otherwise changing the photosensitive material). In certain embodiments, the electromagnetic radiation emitted by the harmonic generation material at the second frequency may disrupt the association between the photosensitive material and the agent, photosensitive material and the harmonic generation material, and/or the harmonic generation material and the agent.

As noted above, in FIG. 1B, absorption of the electromagnetic radiation at the second frequency by the photosensitive material (e.g., bond, linker molecule) results in the cleavage of a chemical bond. In certain embodiments, bond cleavage divides the photosensitive material into at least two separate portions (e.g., a first portion and at least a second, separate portion). In FIG. 1B, first portion 25A of the photosensitive material is associated with (e.g., bound to) the harmonic generation material and second, separate, portion 25B of the photosensitive material is associated with (e.g., bound to) the agent. In certain embodiments, disruption of the association between the harmonic generation and the agent may allow delivery of the agent to a target environment, such as target environment 35 in FIGS. 1A-1B. For instance, breaking at least one chemical bond in the photosensitive material, may lead to the delivery of the agent 30 and the second portion 25B, which is associated with (e.g., bound to) the agent, to a targeted region or site in vivo or in vitro (e.g., receptor, organ, cell, binding site, reaction area).

Figure 2A:
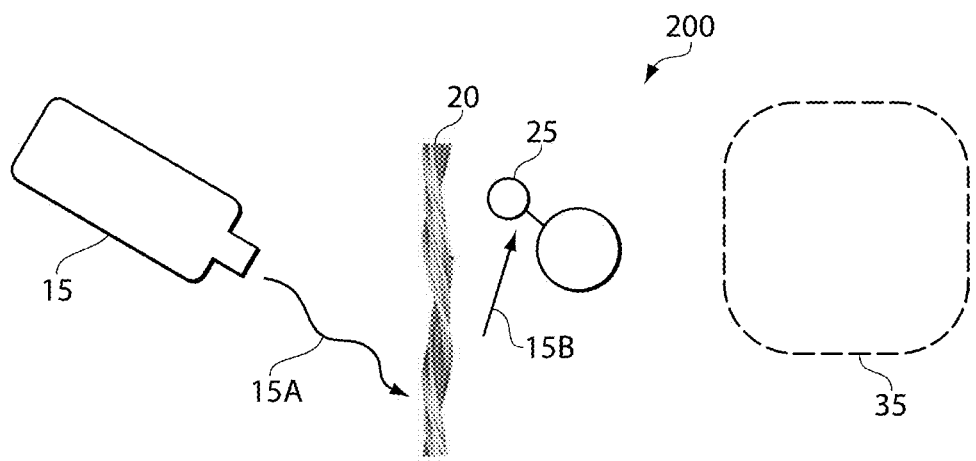
FIGS. 2A-2C are schematic illustrations of a system in which electromagnetic radiation emitted from a harmonic generation material is absorbed by a photosensitive material binding an agent to another molecule, according to some embodiments.
Figure 2B:
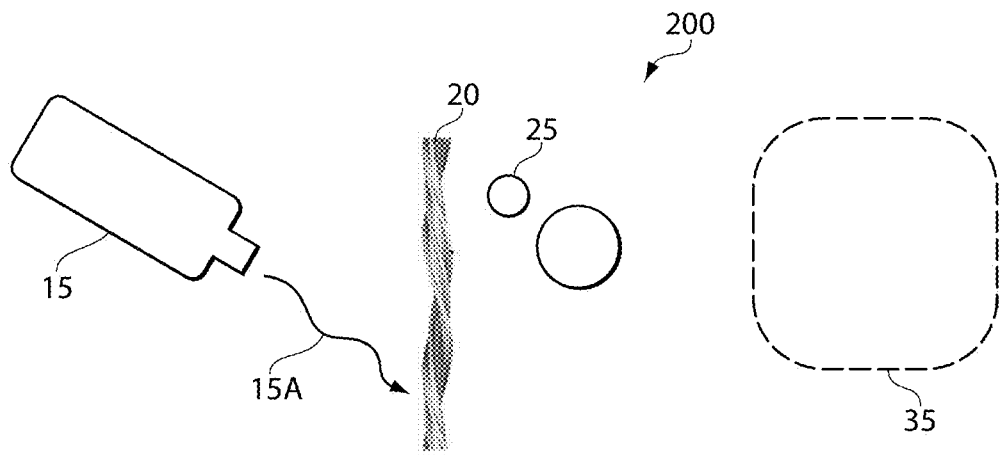
Figure 2C:
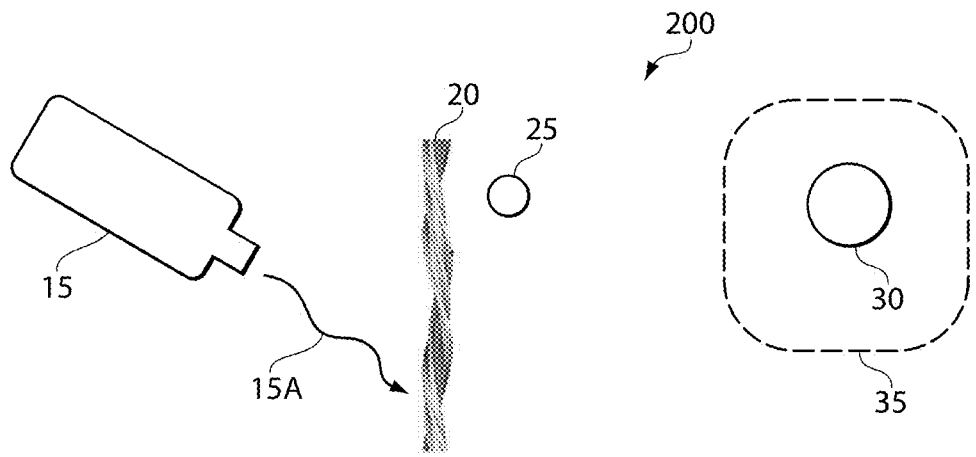

FIGS. 2A-2C are schematic diagrams of another system in which at least one chemical bond of a photosensitive material is broken after the photosensitive material absorbs electromagnetic radiation generated by a harmonic generation material. As illustratively shown in FIG. 2A, system 200 may include harmonic generation material 20 and photosensitive material 25. Unlike FIGS. 1A-1B, in FIGS. 2A-2C, photosensitive material 25 is in close proximity to harmonic generation material 20, but photosensitive material 25 and harmonic generation material 20 are not bonded or otherwise in direct contact (e.g., via a bond or other form of direct contact). Irradiation of harmonic generation material 20 with electromagnetic radiation at a first frequency 15A may result in the release of electromagnetic radiation at a second frequency 15B by the harmonic generation material. As shown in FIG. 2A, photosensitive material 25 is associated with agent 30. The association between the photosensitive material and the agent may cause the agent to be inactive. For example, in FIGS. 2A-2C, photosensitive material 25 serves as a "cage" to prevent agent 30 from forming or undergoing the necessary associations or processes required for activity. As one particular example, the photosensitive material may be bonded to the agent via a moiety which imparts functionality to the agent, and the presence of the photosensitive agent may suppress the functionality of the moiety. As another example, the photosensitive material may physically hinder the interaction of the agent with another molecule (e.g., a receptor). Referring back to FIG. 2B, irradiation of photosensitive material 25 with released electromagnetic radiation 15B may break the association between photosensitive material 25 and agent 30, effectively "uncaging" the agent. In some embodiments, the uncaged agent may form or undergo the necessary associations or processes required for activity. For example, as illustrated in FIG. 2C, the uncaged molecule may freely travel to the target environment 35.

Figure 3A:
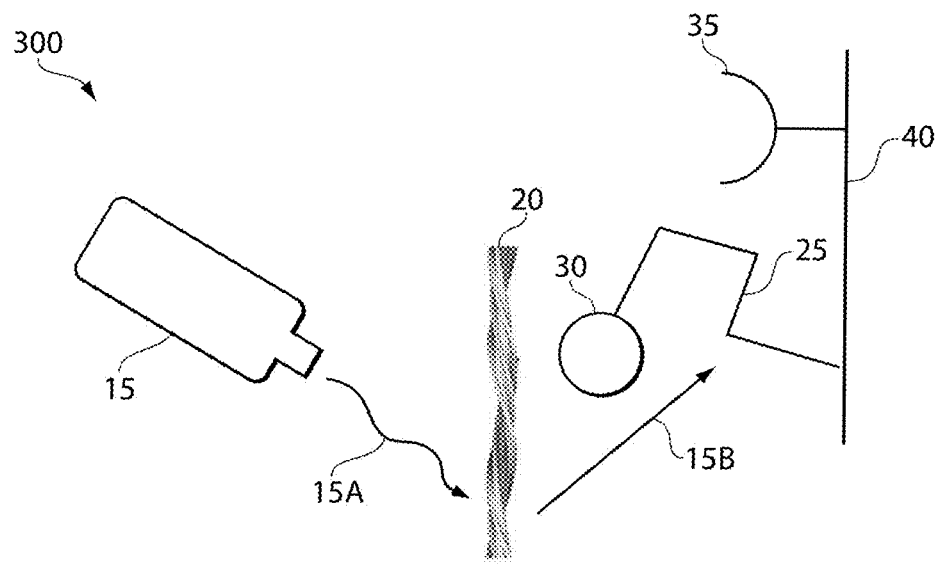
FIGS. 3A-3B are schematic illustrations of a system in which electromagnetic radiation emitted from a harmonic generation material is absorbed by a photosensitive material, resulting in a change in molecular conformation of the photosensitive material, according to certain embodiments.
Figure 3B:
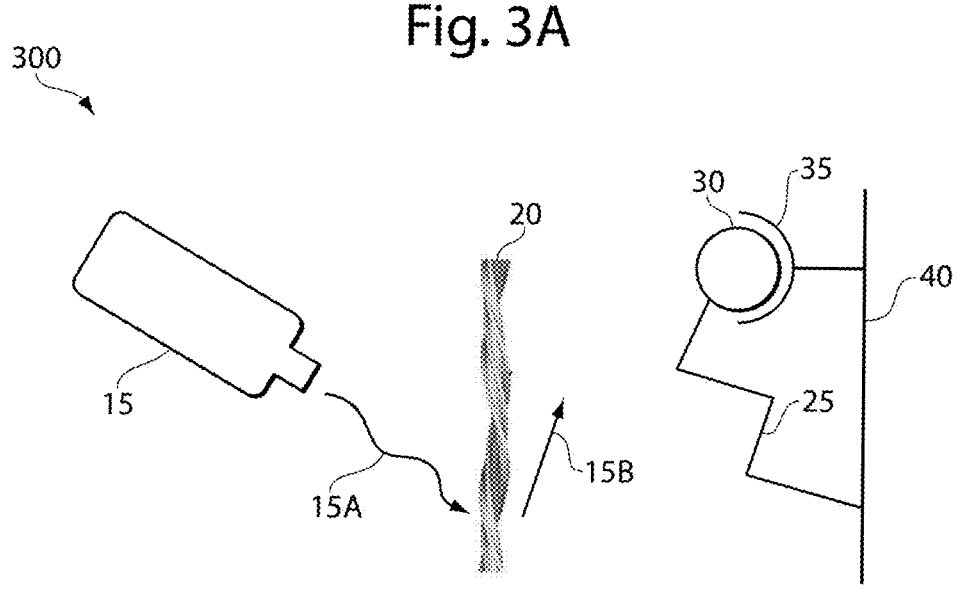

In certain embodiments, when the photosensitive material absorbs the electromagnetic radiation of the second frequency emitted by the harmonic generation material, the molecular conformation of the photosensitive material is altered. Alteration of the molecular conformation of the photosensitive material can occur in addition to or in place of the breaking of a chemical bond within the photosensitive material. FIGS. 3A-3B are schematic diagrams of system 300 in which the molecular conformation of photosensitive material 25 is altered after photosensitive material 25 absorbs electromagnetic radiation generated by harmonic generation material 20. In FIG. 3A, electromagnetic radiation having a first frequency 15A is emitted from source 15 and used to irradiate harmonic generation material 20. Irradiation of harmonic generation material 20 with electromagnetic radiation at a first frequency 15A may result in the release of electromagnetic radiation at a second frequency 15B, to which photosensitive material 25 is sensitive. In some embodiments, as shown in FIG. 3A, photosensitive material 25 may be associated with surface 40 (e.g., via a chemical bond or biological bond). Surface 40 can be positioned or otherwise configured such that it is in close proximity to the harmonic generation material. A target environment (e.g., a receptor) may also be associated with surface 40, in certain embodiments.

In some embodiments, agent 30 may be associated with the photosensitive material. In some such embodiments, prior to exposure of the photosensitive material to electromagnetic radiation 15B, the molecular conformation of the photosensitive material may prevent the agent from interacting with the target environment. In some embodiments, when the electromagnetic radiation at a second frequency 15B emitted by the harmonic generation material 20 is absorbed by photosensitive material 25, the molecular conformation of photosensitive material 25 can be altered. Alteration of the molecular conformation of a photosensitive material may occur via any suitable mechanism. In certain embodiments, altering the molecular conformation of the material comprises rotation around a bond (e.g., cis to trans conversion as illustrated, for example, in FIGS. 3A-3B). In some embodiments, bond formation (e.g., formation of an electrostatic interactions, formation of a hydrogen bond, formation of a Van der Waals interaction) can occur in association with the change in conformation of the photosensitive material.

Figure 4A:
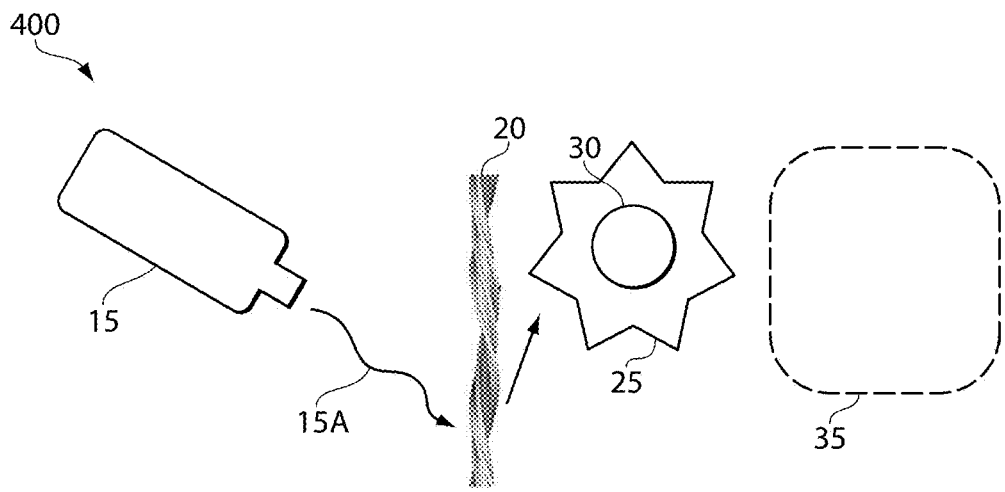
FIGS. 4A-4C are, according to some embodiments, schematic illustrations of a system in which electromagnetic radiation emitted from a harmonic generation material is absorbed by a photosensitive material in which an agent is encapsulated.
Figure 4B:
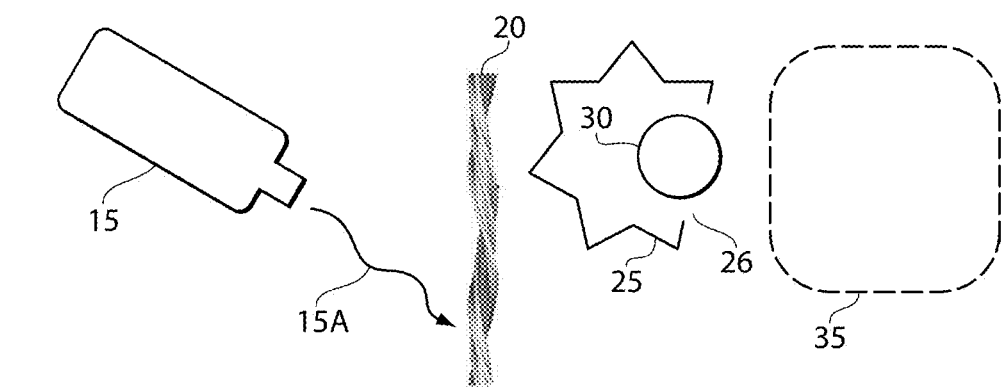
Figure 4C:
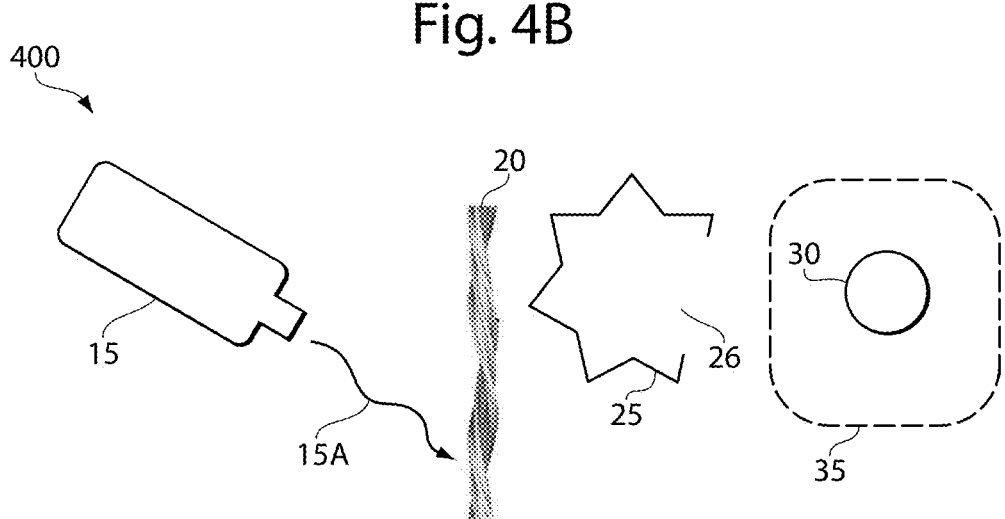

FIGS. 4A-4C are schematic diagrams of another system 400 in which the molecular conformation of photosensitive material 25 is altered after photosensitive material 25 absorbs electromagnetic radiation generated by harmonic generation material 20. In FIG. 4A, photosensitive material 25 at least partially surrounds agent 30. For example, the photosensitive material may be part of a particle and the particle may contain the agent. Photosensitive material 25 can be in the form of, for example, the shell of a core-shell particle and/or the outer layer(s) of a liposome or a micelle. In FIG. 4A, electromagnetic radiation having a first frequency 15A is emitted from source 15 and used to irradiate harmonic generation material 20. Irradiation of harmonic generation material 20 with electromagnetic radiation at a first frequency 15A can result in the release of electromagnetic radiation at a second frequency 15B, to which photosensitive material 25 is sensitive. In FIGS. 4A-4C, photosensitive material 25 encapsulates agent 30. In some embodiments, as shown in FIG. 4B, irradiation of photosensitive material 25 with electromagnetic radiation 15B can cause opening 26 to form within photosensitive material 25 (e.g., due to a change in molecular conformation of the photosensitive material).

A variety of types of molecular conformation change can be used in the systems and methods described herein. In certain embodiments, electromagnetic radiation at the second frequency emitted by the harmonic generation material may cause photoisomerization (e.g., reversible or irreversible photoisomerization) of the photosensitive material. As one such example, ultraviolet electromagnetic radiation can cause photoisomerization of an azobenzene moiety. In some embodiments, electromagnetic radiation at the second frequency emitted by the harmonic generation material may induce a phase transition in the photosensitive material. As one such example, ultraviolet electromagnetic radiation can be used to induce a phase transition within a polymer gel (e.g., a synthetic polymer gel, a natural polymer gel). In certain embodiments, electromagnetic radiation at the second frequency emitted by the harmonic generation material may produce a physical reaction within the photosensitive material (e.g., heat generation, electromagnetic radiation emission, etc.). The physical reaction may in turn produce a chemical or physical alteration in the photosensitive material. As one such example, the photosensitive material may contain moieties (e.g., electromagnetic radiation-absorbing chromophores), which convert electromagnetic radiation into heat. The photosensitive material may also contain thermally responsive moieties (e.g., polymers), which undergo a phase change at the elevated temperatures produced by the heat generation.

In some embodiments, altering the molecular conformation of the photosensitive material may cause an agent associated with the photosensitive material to be released or otherwise transported to a target environment. For example, as illustrated in FIGS. 3A-3B, alteration of the photosensitive material from a first configuration (illustrated in FIG. 3A) to a second configuration (illustrated in FIG. 3B) results in the physical movement of agent 30 into target environment 35 (e.g., a pharmaceutical receptor). As another example, referring to FIG. 4C, alteration of the molecular conformation of photosensitive material 25 creates an opening through which agent 30 can be transported prior to reaching target region 35.

In certain embodiments, irradiation of a photosensitive material may result in more than one alteration in the photosensitive material. In some embodiments, the plurality of alterations may occur in a substantially stochastic, ordered, sequential, or simultaneous manner. For instance, the photosensitive material may undergo a physical change (e.g., change in molecular conformation), which disrupts at least one chemical bond. For example, while the embodiments illustrated in FIGS. 3A-3B and FIGS. 4A-4C have been described as involving a change in the molecular conformation of the photosensitive material, exposure of the photosensitive material to the electromagnetic radiation emitted by the harmonic generation material in the systems of FIGS. 3A-3B and FIGS. 4A-4C may also result in the breaking of at least one chemical bond, in addition to or in place of the change in molecular conformation. As another example, electromagnetic radiation at a reactive wavelength may initiate an ionization reaction in the photosensitive material (which might involve the breaking of at least one chemical bond), which creates osmotic pressure inside the photosensitive material that may lead to swelling of the photosensitive material (a change in molecular conformation).

The harmonic generation material and the photosensitive material can be brought into close proximity (e.g., as illustrated in FIGS. 1A-1B, FIGS. 2A-2C, FIGS. 3A-3B, and FIGS. 4A-4C, as well as in other embodiments) via a variety of mechanisms. In certain embodiments, a photosensitive material (optionally, associated with an agent) can be introduced to an environment in which the harmonic generation material is present. As one such example, collagen can be used as the harmonic generation material, and the photosensitive material (optionally, along with an agent) can be introduced into a subject in which collagen is present. Collagen is ubiquitous in many animals, including humans. Accordingly, in certain embodiments, the photosensitive material can be introduced to an animal subject. Any suitable introduction pathway can be used, including but not limited to, introduction through the eye, the gastrointestinal tract, injection into the bloodstream, or any other suitable pathway. The photosensitive material introduced into the subject (optionally in association with an agent) can naturally associate with the collagen within the subject, for example, as the photosensitive material is distributed via the bloodstream. Subsequently, the subject can be exposed to electromagnetic radiation having a first frequency, which can interact with the collagen to produce electromagnetic radiation having a second, higher frequency, which can alter the photosensitive material and activate, deliver, or release the agent.

As another example, the harmonic generation material and the photosensitive material can be part of a particle. In some such embodiments, the harmonic generation material and the photosensitive material are chemically bonded to each other within the particle. In certain embodiments, one of the harmonic generation material and the photosensitive material is at least partially surrounded by the other. The harmonic generation material and the photosensitive material may also be associated with each other via any other chemical, physical, or biological interaction. An agent may also be part of the particle (e.g., chemically bonded to the harmonic generation material and/or the photosensitive material, at least partially surrounded by the harmonic generation material and/or the photosensitive material, or otherwise associated with the harmonic generation material and/or the photosensitive material, for example, via a chemical, physical, or biological interaction). The particles can be of any suitable size. In certain embodiments, the particles have maximum cross-sectional dimensions of less than about 1 millimeter, less than about 100 microns, less than about 10 microns, less than about 1 micron, less than about 100 nanometers, or less than about 10 nanometers. In certain embodiments, the particles can be formed outside a subject and be subsequently introduced into a subject. For example, the particles may be part of a suspension or other pharmaceutically acceptable carrier that can be delivered to a subject. The particles may be delivered to the subject via any suitable pathway, including via the gastrointestinal tract, via the eye, via injection into the bloodstream, or using any other introduction pathway. The particles can be distributed through the body of the subject, for example, via the bloodstream. Subsequently, the subject can be exposed to electromagnetic radiation having a first frequency, which can interact with the harmonic generation material within the particle to produce electromagnetic radiation having a second, higher frequency, which can alter the photosensitive material within the particle (and optionally activate, deliver, or release an agent).

In certain embodiments, targeted activation, delivery, or release of an agent can be achieved by directing the electromagnetic radiation having the first, relatively low frequency (e.g., infrared electromagnetic radiation) only to certain regions (e.g., to specific locations within a subject) in which alteration of the photosensitive material and/or delivery, activation, or release of the agent is desired. In some such embodiments, when the electromagnetic radiation having the first, relatively low frequency is directed only to a specified region, only the harmonic generation material within the exposed region is triggered to generate electromagnetic radiation having a second, higher frequency. In turn, in some such embodiments, only the photosensitive material within the exposed region is altered, and, in such embodiments in which an agent is present, only the agent within the exposed area is activated, released, or otherwise delivered. Such targeted delivery of agents can have a variety of applications. For example, in certain embodiments, the agent may correspond to a cancer drug. In some such embodiments, the cancer drug can be delivered to a subject in an inactive form, and subsequently, the subject can be exposed to low-energy electromagnetic radiation (e.g., infrared electromagnetic radiation) only within regions in which activation of the cancer drug is desirable (e.g., at the tumor site). As another example, the agent may correspond to an photoluminescent particle or other imaging material that has been delivered to the subject. In some such embodiments, the imaging material can be delivered to a subject in an inactive form, and subsequently, the subject can be exposed to low-energy electromagnetic radiation (e.g., infrared electromagnetic radiation) only within regions in which it is desirable to produce an image of the subject.

A variety of harmonic generation materials can be used in association with the embodiments described herein. As described above, harmonic generation materials generally induce interactions between two or more incident photons and produce one or more new photons with higher frequencies and energies and shorter wavelengths than the original incident photons. For example, in the case of second harmonic generation, exposing the harmonic generation material to electromagnetic radiation may cause the incident photons to combine and generate new photons with half the wavelength and twice the frequency as the original incident photons. In the case of third harmonic generation, the harmonic generation material may generate photons with one third of the wavelengths and three times the frequencies of the incident photons. In general, any order harmonic generation material may be used to convert incident electromagnetic radiation at one frequency to released electromagnetic radiation at another frequency. For instance, in some embodiments, high harmonic generation material (e.g., nth harmonic generation material where n is equal to or greater than 3 and, in certain embodiments, less than or equal to 100) may be used. In some embodiments, the harmonic generation material can be configured to participate in second harmonic generation and/or third harmonic generation. In some cases, the harmonic generation material can be configured to participate in second harmonic generation.

In some embodiments, incident electromagnetic radiation may undergo one or more harmonic generation processes in the harmonic generation material before being released. For example, in some embodiments, infrared electromagnetic radiation may undergo a second or third harmonic generation processes to release ultraviolet electromagnetic radiation (e.g., 10 nm to 380 nm). In another example, near infrared electromagnetic radiation (e.g., 800 nm to 2,500 nm) may undergo a higher order harmonic generation process (e.g., fourth, fifth, sixth, seventh, eighth, ninth, tenth, etc.) to generate ultraviolet electromagnetic radiation (e.g., 10 nm to 380 nm) and/or visible electromagnetic radiation (e.g. 380 nm to 780 nm). In certain embodiments in which the incident electromagnetic radiation undergoes high harmonic generation processes before electromagnetic radiation is released by the harmonic generation material, the electromagnetic radiation may undergo less than or equal to 100, less than or equal to 75, less than or equal to 50, less than or equal to 25, less than or equal to 10, less than or equal to 5, less than or equal to 3, or less than or equal to 2 harmonic generation processes. In general, electromagnetic radiation incident on the harmonic generation material may participate in any suitable number of harmonic generation processes before electromagnetic radiation at a second frequency is emitted by the harmonic generation material.

In some embodiments, the harmonic generation material may release electromagnetic radiation (which can, in certain embodiments, be absorbed or otherwise interact with the photosensitive material) with at least one wavelength less than or equal to 780 nm, less than or equal to 700 nm, less than or equal to 600 nm, less than or equal to 500 nm, less than 380 nm, less than or equal to 320 nm, less than or equal to 240 nm, less than or equal to 180 nm, less than or equal to 120, or less than or equal to 60 nm. In certain embodiments, the harmonic generation material may release electromagnetic radiation (which can, in certain embodiments, be absorbed or otherwise interact with the photosensitive material) with at least one wavelength greater than or equal to 10 nm, greater than or equal to 80 nm, less than or equal to 150 nm, greater than or equal to 220 nm, greater than or equal to 280 nm, greater than or equal to 365 nm, greater than or equal to 460 nm, greater than or equal to 560 nm, or greater than or equal to 660 nm. Combinations of the above-referenced ranges are also possible (e.g., greater than or equal to 10 nm and less than 380 nm, etc.). The release of electromagnetic radiation, by the harmonic generation material, having wavelengths with other values is also possible.

It should be understood that, while many materials may exhibit harmonic generation properties when exposed to electromagnetic radiation at very high intensities, the use of such materials requiring high intensity electromagnetic radiation sources and may not be suitable for certain applications. Thus, in some embodiments, the harmonic generation material can be capable of converting electromagnetic radiation of a first frequency (e.g., an infrared or near infrared frequency or a frequency within any of the other ranges described herein) to electromagnetic radiation of the second, higher frequency (e.g., an ultraviolet frequency or a frequency within any of the other ranges described herein) at an efficiency of at least about $10^{-10}$, at least about $10^{-8}$, at least about $10^{-6}$, at least about $10^{-4}$, or at least about $10^{-2}$ when illuminated with electromagnetic radiation of the first frequency at an intensity of $10^{11}$ W/cm$^2$. In certain embodiments, the harmonic generation material may be capable of conversion efficiencies of up to 0.1 when illuminated with electromagnetic radiation of the first frequency at an intensity of $10^{11}$ W/cm$^2$. The efficiency with which a harmonic generation material converts incoming electromagnetic radiation of a first frequency to electromagnetic radiation of a second, higher frequency is generally calculated by dividing the intensity at which the harmonic generation material emits electromagnetic radiation of the second frequency from its surface by the intensity at which the surface of the harmonic generation material is exposed to electromagnetic radiation of the first frequency. The intensity to which the surface of the harmonic generation material is exposed can be determined by using a source with a known emission intensity (e.g., determined by calibrating the source with a spectrometer), using equations known to those of ordinary skill in the art to account for any dissipation of intensity between the source and the harmonic generation material. The intensity with which the harmonic generation material emits electromagnetic radiation of the second frequency can be determined by direct measurement of the emitted intensity using a spectrometer or other suitable instrument, using equations known to those of ordinary skill in the art to account for any dissipation of intensity between the harmonic generation material and the spectrometer. In some embodiments, suitable harmonic generation materials for use in association with certain inventive systems and methods described herein can be selected using a screening test in which the conversion efficiency of the harmonic generation material is determined and compared to a minimum desirable conversion efficiency. For example, the potential harmonic generation material can be exposed, in certain embodiments, to electromagnetic radiation having a first frequency (e.g., an infrared frequency) at an intensity of $10^{11}$ W/cm², and the amount of electromagnetic radiation having a second, higher frequency that is generated by the harmonic generation material (e.g., the amount of ultraviolet electromagnetic radiation generated by the harmonic generation material) can be measured. In some embodiments, if the conversion efficiency of the tested harmonic generation material is at least about $10^{-10}$ (or, in certain embodiments, at least about $10^{-8}$, at least about $10^{-6}$, at least about $10^{-4}$, or at least about $10^{-2}$) when illuminated with electromagnetic radiation of the first frequency at an intensity of $10^{11}$ W/cm², the harmonic generation material can be selected for use in the system.

In general, any non-centrosymmetric and/or frequency-multiplying material may be used as a harmonic generation material. Non-limiting examples of harmonic generation materials include collagen (e.g., endogenous or exogenous collagen), myosin (e.g., endogenous or exogenous myosin), $LiNbO_3$, $BaTiO_3$, $KTiO_3$, $KTiOPO_4$, $LiB_3O_5$, ammonium dihydrogen phosphate, $KH_2PO_4$, MgO, $KNbO_3$, $\beta$-$BaB_2O_4$, and $LiIO_3$, and combinations thereof. In some embodiments, the harmonic generation material can comprise cellular membranes and/or cellulose. In certain embodiments, harmonic generation materials may be selected based on their efficiency and accessibility. For instance, collagen and/or myosin may be used as a harmonic generation material (e.g., a second harmonic generation material) due to their high efficiency and relative abundance within certain environments, such as within animal subjects. In some cases, the presence of collagen and/or myosin in vivo may be exploited for use in the harmonic generation-triggering system. In other cases, exogenous collagen/and or myosin may be utilized. In certain embodiments, high efficiency inorganic harmonic generation material, such as $LiNbO_3$ and $BaTiO_3$, may be also used. Other harmonic generation materials may also be used. Suitable harmonic generation materials for use in the inventive systems and processes described herein can be selected readily by those of ordinary skill in the art, given the description herein.

In various embodiments, electromagnetic radiation released by a harmonic generation material may be used to induce a change in a photosensitive material. Generally, the photosensitive material can be any material (e.g., atom, small molecule, macromolecule, system of molecules, macromolecular structure, supramolecular structure, network) that undergoes a chemical and/or physical alteration (e.g. chemical reaction, change in molecular conformation) upon absorbing electromagnetic radiation (e.g., electromagnetic radiation at a first frequency emitted by the harmonic generation material). In some embodiments, the photoactive material may undergo a chemical alteration in response to electromagnetic radiation released from the harmonic generation material. The photosensitive material may undergo a variety of chemical alterations. For example, in some embodiments, at least one bond (e.g., chemical or biological) in the photosensitive material may be broken upon exposure of the photosensitive material to the electromagnetic radiation. As one particular example, a nitrobenzyl linkage may be cleaved in the presence of electromagnetic radiation, for example, having a wavelength of 365 nm. In certain embodiments, at least one bond may be formed in the photosensitive material due to irradiation by electromagnetic radiation emitted by the harmonic generation material. For instance, absorption of electromagnetic radiation by the photosensitive material may lead to molecular rearrangement, in which a new chemical and/or biological interaction (e.g., electrostatic interactions, hydrogen bonding, biological binding events) is produced.

A wide variety of photosensitive materials may be used. In some embodiments, the photosensitive material may be selected based on its sensitivity to a specific wavelength and/or intensity of electromagnetic radiation. The photosensitive material may also be selected based on characteristics important for its intended application (e.g., low toxicity, biocompatibility, in vivo clearance, and the like). Exemplary types of photosensitive material include particles (e.g., nanoparticles, microparticles), biomaterials, linker molecules, small molecules, functional groups, bonds, liposomes, micelles, nucleic acids (e.g., DNA, RNA, siRNa, aptamers), networks (e.g., polymeric networks), and combinations thereof. The photosensitive material may include a single type of photosensitive material or a combination of multiple types of photosensitive materials.

Non-limiting examples of photosensitive molecular structures that the photosensitive material may comprise include azobenzenes, o-nitrobenzyls, coumarins, phenacyl groups, benzoin esters, desyl compounds, arylazidoalcohols, nitroveratryloxycarbonyl (NVOC), 2-(dimethylamino)-5-nitrophenyl (DANP), Bis(o-nitrophenyl)ethanediol, brominated hydroxyquinoline, dinitrobenzenesulfenyl esters, nitroindolines, o-nitrophenylene glycols, dithianes, bezyl alcohols, sulphonamides, polycyclic aromatic hydrocarbons, carbamates, and combinations thereof. Photosensitive moieties suitable for use in the embodiments described herein can be selected readily by those of ordinary skill in the art, when provided the present disclosure.

As described elsewhere, certain of the harmonic generation-based triggering systems described herein include an agent. Suitable agents include any functional molecule, the delivery or activity of which can influence a target environment. The agent may be active (i.e., capable of influencing its target environment) or inactive. Inactive agents (e.g., pro-drugs) may be produced by associating an active agent with a molecule or group of molecules that adversely affects an element of the agent that is essential for activity.

In some embodiments, the agent may be a pharmaceutical composition such as, for example, small molecule drugs, proteins, nucleic acids, polysaccharides, and/or biologics. The agent may be any compound capable of providing a therapeutic benefit. Pharmaceutical agents (e.g., drugs) may be selected from small molecules, organic compounds, inorganic compounds, proteins, nucleic acids, and/or carbohydrates. In certain embodiments, the pharmaceutical agent comprises a growth factor, an angiogenic agent, an anti-inflammatory agent, an anti-infective agent (e.g., an antibacterial agent, antiviral agent, antifungal agent, and/or an agent that inhibits protozoan infections), an antineoplastic agent, and anesthetic agent, an anti-cancer composition, an autonomic agent, a steroid (e.g., a corticosteroid), a non-steroidal anti-inflammatory drug (NSAID), an antihistamine, a mast-cell stabilizer, an immunosuppressive agent, and/or an anti-mitotic agent. In certain embodiments, the agent may be a virus and/or cell. In some cases, a virus may be used for gene delivery. Gene delivery may be beneficial, for example, for regenerative medicine. A cell may be used, in some instances, as an active agent factory. For example, a cell (i.e., a stem cell) may secrete a growth factor or other agent that has therapeutic value. These cells may continuously generate and deliver a therapeutic. In certain embodiments, the pharmaceutical composition may be selected from "Approved Drug Products with Therapeutic Equivalence and Evaluations," published by the United States Food and Drug Administration (F.D.A.) (the "Orange Book").

In other embodiments, the agent may not be therapeutically active. For example, the agent may comprise a photoluminescent molecule, such as a dye, a fluorescent molecule, or another photoluminescent molecule. In embodiments in which the agent is a dye, the dye may be used for in vitro imaging. In certain instances, the dye may be used in diagnostic and/or sensor applications, such as nucleic acid assays and protein assays.

In embodiments in which the harmonic generation based triggering systems are used in association with pharmaceutical compositions (or pharmaceutically acceptable compositions), the pharmaceutical composition can comprise a therapeutically effective amount of an active agent formulated together with one or more pharmaceutically acceptable carriers, additives, and/or diluents. The pharmaceutical compositions described herein may be useful for diagnosing, preventing, treating or managing a disease or bodily condition. Pharmaceutically acceptable compositions can include, for example, structures, materials, compositions, and/or dosage forms which are, within the scope of sound medical judgment, suitable for use in contact with the tissues of human beings and/or animals without excessive toxicity, irritation, allergic response, or other problem or complication, commensurate with a reasonable benefit/risk ratio. Pharmaceutically-acceptable carriers can include, in certain embodiments, materials, compositions, or vehicles (e.g., a liquid, gel or solid filler, diluent, excipient, or solvent encapsulating material) which can be involved in carrying or transporting an active compound (e.g., from a device or from one organ, or portion of the body, to another organ, or portion of the body). Generally, acceptable carriers are those which are compatible with other ingredients of the formulation and not injurious to the subject.

As noted above, various harmonic generation based triggering systems can include a harmonic generation material and a photosensitive material (and, in certain embodiments, an optional agent) associated with each other. The association between the harmonic generation material and the photosensitive material (and/or between the harmonic generation material and the optional agent and/or between the photosensitive material and the optional agent) can be of any suitable type. For example, the association between the harmonic generation material and the photosensitive material (and/or between the harmonic generation material and the optional agent and/or between the photosensitive material and the optional agent) can comprise a chemical interaction, a physical interaction, a biological interaction, and/or a close-proximity spatial orientation.

In certain embodiments, one or more of the harmonic generation material, the photosensitive material, and the optional agent may be associated with another of these components via a physical interaction. For example, in some embodiments the harmonic generation material (e.g., collagen fibers, collagen polymer) may be physically entangled with at least a portion of the photosensitive material (e.g., photoactive polymer). In some embodiments, the agent may be physically entangled with at least a portion of the harmonic generation material and/or the photosensitive material.

In some embodiments, two or more components may associate via a chemical interaction, such as a chemical bond. The chemical bond may be a covalent bond or non-covalent bond. In some cases, the chemical bond is a non-covalent bond such as a hydrogen bond, ionic bond, dative bond, and/or a Van der Waals interaction. One or more of the harmonic generation material, the photosensitive material, or the optional agent may comprise functional groups capable of forming such bonds. For example, a component (e.g., harmonic generation material) may include at least one hydrogen atom capable of interacting with a pair of electrons on a hydrogen-bond acceptor of another components (e.g., a photosensitive material and/or an agent) to form the hydrogen bond. In some embodiments, the harmonic generation material, the photosensitive material, and/or the optional agent may include an electron-rich or electron-poor moiety, such that it may form an electrostatic interaction with another of the harmonic generation material, the photosensitive material, and/or the optional agent. It should be understood that covalent and non-covalent bonds between components may be formed by any type of reactions, as known to those of ordinary skill in the art, using the appropriate functional groups to undergo such reactions. Chemical interactions suitable for use with various embodiments described herein can be selected readily by those of ordinary skill in the art, based upon the description herein.

In some embodiments, an association between a harmonic generation material and a photosensitive material (and/or between a harmonic generation material and an agent and/or between a photosensitive material and an agent) may occur via a biological binding event (i.e., between complementary pairs of biological molecules). For example, a component (e.g., a harmonic generation material, a photosensitive material, and/or an agent) may include an entity such as biotin that specifically binds to a complementary entity, such as avidin or streptavidin, on another component (e.g., a harmonic generation material, a photosensitive material, and/or an agent). Other examples of biological molecules that may form biological bonds between pairs of biological molecules include, but are not limited to, proteins, nucleic acids, glycoproteins, carbohydrates, hormones, and the like. Specific examples include, but are not limited to, an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Biological interactions between the harmonic generation material and the photosensitive material (and/or between these components and an agent) suitable for use in the embodiments described herein can be selected readily, by those of ordinary skill in the art, based upon the description herein as their function, examples of such biological interactions, and knowledge herein and in the art as to simple techniques for identifying suitable chemical interactions.

In certain embodiments, the harmonic generation material can be in close proximity to the photosensitive material, the optional agent can be in close proximity to the photosensitive material, and/or the optional agent can be in close proximity to the harmonic generation material. For example, in some embodiments, the shortest distance between the harmonic generation material and the photosensitive material (and/or the shortest distance between the harmonic generation material and the optional agent, and/or the shortest distance between the photosensitive material and the optional agent) may be less than or equal to 1 centimeter, less than or equal to 1 millimeter, less than or equal to 100 micrometers, less than or equal to 10 micrometers, less than or equal to 1 micrometer, less than or equal to 100 nanometers, or less than or equal to 10 nanometers. In certain embodiments, the shortest distance between the harmonic generation material and the photosensitive material (and/or the shortest distance between the harmonic generation material and the optional agent, and/or the shortest distance between the photosensitive material and the optional agent) is greater than or equal to 1 nanometer, greater than or equal to 10 nanometers, or greater than or equal to 100 nanometers. Combinations of the above-referenced ranges are also possible (e.g., greater than or equal to 1 nanometer and less than 1 centimeter). In some embodiments, the harmonic generation material and the photosensitive material can be in direct contact. In certain embodiments, the optional agent can be in direct contact with the harmonic generation material and/or the photosensitive material.

In certain embodiments, one of the harmonic generation material, the photosensitive material, and the optional agent may at least partially (or substantially completely) surround another of these components. For example, a photosensitive material may at least partially surround an agent and/or harmonic generation material. In another example, a harmonic generation material may at least partially surround a photosensitive material and/or an agent.

The harmonic generation-based triggering systems described herein may be used in a variety of applications, including in drug delivery, imaging, diagnostics, and sensing, among others. In certain embodiments, the harmonic generation-based triggering systems described herein may be used in association with biomedical implants, medical devices, and/or electronic systems. In certain embodiments, a particle (e.g., comprising a harmonic generation material, a photosensitive material, and, optionally, an agent) may be used in the harmonic generation-based triggering systems for various applications. The particle may be a micelle (e.g., copolymer micelle), for example, having a hydrophobic core and a hydrophilic shell. The core may contain a photosensitive material (e.g., photocleavable moieties) and an agent. Irradiation of the particle at an appropriate frequency (e.g., an ultraviolet frequency) may cause the core to become hydrophilic, which dissociates the micelle, and releases the agent. In another embodiment, the particle may be a nanoparticle (e.g., polymer nanoparticle) that comprises an agent. The nanoparticle may contain a photosensitive material, such that irradiation at an appropriate wavelength induces a change in molecular conformation (e.g., an increase and/or decrease in particle size) and releases the agent.

In one set of embodiments, harmonic generation materials, such as inorganic non-centrosymmetric nanocrystals (e.g., $LiNbO_3$, $BaTiO_3$) may be encapsulated (e.g., in the core) of a photosensitive particulate carrier (e.g., micelle, liposome) along with an agent. In some embodiments, the photosensitive particulate carrier may include a shell comprising a photosensitive material. The harmonic generation material can efficiently convert incident electromagnetic radiation at a first frequency (to which the photosensitive material is not substantially sensitive) into electromagnetic radiation having a second, higher frequency (to which the photosensitive material is sensitive) such that a chemical or physical change occurs in the photosensitive particulate carrier. Irradiation of the particle with electromagnetic radiation at the first frequency can result the harmonic generation material within the particle producing electromagnetic radiation of the second frequency, which can be absorbed by the photosensitive material and result in the release of the agent. In some embodiments, the agent may be bound to a particle (e.g., polymer nanoparticle), which contains a harmonic generation material via a photosensitive linker. Irradiation of the particle with electromagnetic radiation at a first frequency can result in the harmonic generation material emitting electromagnetic radiation having a second, higher frequency, which can be absorbed by the photosensitive material and result in the release of the agent.

In embodiments, in which the agent is a pharmaceutical agent and/or photoluminescent molecule, such particles may be used, for example, in drug delivery, imaging, and biomedical implants. For instance, the particles may be used in remotely triggerable drug delivery systems. For in vivo applications, drug release may be triggered by exposing the target environment to low energy electromagnetic radiation, such as near infrared or infrared. The harmonic generation materials in the particle (e.g., $BaTiO_3$, $LiNbO_3$, collagen, myosin) and/or naturally occurring in vivo (e.g., collagen, myosin) may convert incoming electromagnetic radiation to electromagnetic radiation having a higher energy, which can subsequently be absorbed by photosensitive material and cause local release of an agent.

In certain embodiments, similar methods may be used for imaging and biomedical implant applications. In imaging, the agent may be an inactive photoluminescent molecule. In certain embodiments, the electromagnetic radiation that is absorbed by the photosensitive material (which can be emitted by the harmonic generation material), and which is used to release the photoluminecent molecule from the particle, may also be used to activate the photoluminescent molecule. In some embodiments, a biomedical implant or other biomedical device may contain a plurality of particles (e.g., distributed in the implant or device or distributed on the surface of the implant or device). Irradiation at the appropriate wavelength may release the agent from the particle and the biomedical implant. In some instances, the harmonic generation-based triggering system may be reusable (i.e., capable of being triggered more than one time to produce a desired effect). Other applications for particles are also possible, including applications in which the agent is not a pharmaceutical or dye.

In one set of embodiments, one or more components of the harmonic generation-based triggering system may be associated with a surface. For example, FIGS. 3A-3B are schematic illustrations of one set of embodiments in which the photosensitive material is bound to a surface (e.g., surface 40), for example, via a chemical bond. In certain cases, one or more component (e.g., harmonic generation material, photosensitive material, agent) may be directly or indirectly bound to a surface (e.g., a surface of a material that is not part of the harmonic generation material, the photosensitive material, or the agent). For example, in certain embodiments, the harmonic generation material, the photosensitive material, and/or the agent may be bound to one or more tissue surfaces (e.g., muscle tissue surfaces, bone tissue surfaces, cartilage, ligaments, and the like). The harmonic generation material, the photosensitive material, and/or the agent may be bound to the surface by a variety of arrangements. For example, the harmonic generation material may be bound to a surface by a photostable or photosensitive linker. In other cases, one or more components may be associated with the surface via a spatial relationship, which allows close proximity to a surface (e.g., components in a coating on the surface).

In certain embodiments in which one or more components of the harmonic generation-based triggering system is associated with a surface, the harmonic generation-based triggering system may be used in variety of applications, including diagnostics, sensors, medical devices, and electronics. For instance, in certain embodiments in which the triggering system is part of a sensor and/or diagnostic system, a harmonic generation-based triggering system may be used to detect an analyte. Ligands, which bind to the analyte, may be associated with a surface and a photosensitive material (e.g., photocleavable cage molecule), which inactivates the ligand. Irradiation of the surface with a frequency to which the photosensitive material is sensitive may activate the ligand and allow detection of the analyte. In certain embodiments, a similar system may be used in an electronic application. For example, photosensitive material may be associated with a surface and an agent. The photosensitive material and the agent may act as a photosensitive switch and/or valve, such that irradiation of the photosensitive material at a reactive frequency turns on or off the switch and/or valve. In some instances, the switch and/or valve mechanism may be reversible, such that removing the source of reactive electromagnetic radiation may allow the switch and/or valve to return to its original state. In another example, one or more component of the harmonic generation-based triggering system may be including in a coating for a medical device. Irradiation of the coating with a frequency to which the photosensitive material is sensitive may alter the properties of the coating (e.g., surface chemistry, biocompatibility, adhesion properties, etc.) and/or cause an agent to be released. In some instances, the harmonic generation-based triggering system may be reusable. In certain cases, the harmonic generation material may be supplied by the environment in which the system is placed (e.g., inside the human body, on skin, the surface). Other applications for harmonic generation-based triggering system associated with a surface are also possible.

In one set of embodiments, a photosensitive material or harmonic generation, either alone or in association with an agent, may be used in drug delivery applications. In some embodiments, the harmonic generation material may be positioned in or delivered to an environment that contains a photosensitive material associated with an agent, such as a pharmaceutical agent. For example, prior to delivery or positioning of the harmonic generation material, drug that is caged by a photosensitive material may be inside the human body (e.g., free or associated with a matrix or carrier). The location of the photosensitive material associated with an agent may be the target environment for the harmonic generation material. Delivery of the harmonic material to the target environment and irradiation by electromagnetic radiation may activate the drug inside the body. In some instances, the harmonic generation material may be functionalized with moieties the allow localization of the harmonic generation material to the target environment. In another example, a drug caged by a photosensitive material may be delivered to a target environment (e.g., in the inside or outside of human being) that is in close proximity to collagen and/or myosin. Irradiation of the target environment with inert electromagnetic radiation may un-cage and activate the drug.

In certain embodiments, the photosensitive material may be capable of therapeutic activity. In some such embodiments, presence of an agent separate from the photosensitive material is not necessary to effect therapeutic activity. In some such embodiments, irradiation of the photosensitive material at an appropriate wavelength (e.g., a wavelength of electromagnetic radiation emitted by the harmonic generation material) may activate the photosensitive material, for example, by changing the molecular conformation of the photosensitive material to an active conformation. In some such embodiments, the photosensitive material, alone, may be delivered to or positioned in a target environment (e.g., skin) that contains or is in close proximity to a harmonic generation material. In some cases, the photosensitive material associated with a harmonic generation material may be delivered to or positioned within a target environment. In some embodiments, a bodily tissue (e.g., cornea, tendons, cartilage, etc.) may act as a reservoir for an agent associated with a harmonic generation material and/or a photosensitive material that is capable of therapeutic activity. Irradiation of the bodily tissue (e.g., with near infrared or infrared radiation) may cause the harmonic generation material to release higher-energy electromagnetic radiation that activates the photosensitive material and produces a therapeutic effect. The bodily tissue may be irradiated more than one time, or over time, to produce the therapeutic effect. In certain instances, a biomaterial or medical device may act as a reservoir for a photosensitive material associated with a photosensitive material that is capable of therapeutic activity. Other applications for a photosensitive material or harmonic generation, either alone or in association with an agent are also possible.

As described above, a source (e.g., source 15 in FIGS. 1A-1B, 2A-2C, 3A-3B, and 4A-4C) may be used to generate the relatively low-energy electromagnetic radiation used in the harmonic generation-based triggering system. In certain embodiments, the source is configured to emit electromagnetic radiation of the first frequency (i.e., the electromagnetic radiation having the relatively low frequency and energy and relatively large wavelength) such that the electromagnetic radiation of the first frequency is incident upon the harmonic generation material. This can be achieved, for example, by orienting the source such that electromagnetic radiation is emitted in the direction of the harmonic generation material. In certain embodiments, the source is positioned such that the closest distance between the source and the harmonic generation material is about 10 meters or less, about 5 meters or less, about 1 meter or less, or about 10 cm or less.

In general, any electromagnetic radiation source can be used. In some embodiments, the electromagnetic radiation source is configured to emit electromagnetic radiation of the first (relatively low) frequency at an intensity of greater than or equal to about 1 mW/cm$^2$ or greater than or equal to about 1 W/cm$^2$. Non-limiting examples of electromagnetic radiation sources include lasers (e.g., continuous wave lasers, pulsed lasers, and/or supercontinuum lasers), light emitting diodes, and combinations thereof.

In some instances, the frequency and/or intensity of the electromagnetic radiation emitted by the harmonic generation material may be controlled, at least in part, through appropriate selection of the source. For instance, exposing a harmonic generation material (e.g., second harmonic generation material) to a source producing a first frequency that includes at least one infrared frequency may result in the harmonic generation material emitting electromagnetic radiation of a second frequency that includes at least one ultraviolet frequency (e.g., via a second harmonic generation process, via a third harmonic generation process, via a higher order harmonic generation process).

In some embodiments, the electromagnetic radiation source may produce electromagnetic radiation at a single wavelength (e.g. using a laser). In other cases, the electromagnetic radiation source may produce more than one wavelength of electromagnetic radiation. For example, an electromagnetic radiation source may produce a broad or narrow range of wavelengths. The wavelength range may be produced by a single source, in some embodiments, or a combination of sources, in other embodiments. In certain embodiments, a combination of lasers (e.g., continuous wave laser, pulsed laser, and/or supercontinuum lasers) may be used to produce a plurality of wavelengths with a narrow or broad range. Those of ordinary skill in the art, given the present disclosure, would be capable of selecting suitable electromagnetic radiation sources (or combinations of sources) suitable for achieving the triggering effects described herein.

In some embodiments, the electromagnetic radiation source may produce electromagnetic radiation with at least one wavelength greater than or equal to about 700 nm, greater than or equal to about 730 nm, greater than or equal to about 900 nm, greater than or equal to about 1000 nm, greater than or equal to about 1250 nm, greater than or equal to about 1500 nm, greater than or equal to about 1750 nm, or greater than or equal to about 2000 nm. In some instances, the electromagnetic radiation source may produce electromagnetic radiation with at least one wavelength less than or equal to about 2500 nm, less than or equal to about 2250 nm, less than or equal to about 1900 nm, less than or equal to about 1600 nm, less than or equal to about 1300 nm, less than or equal to about 1000 nm, less than or equal to about 900 nm, less than or equal to about 800 nm, or less than or equal to about 750. Combinations of the above-referenced ranges are also possible (e.g., greater than or equal to about 700 nm and less than about 2500 nm, or any other combination of the ranges listed above).

It should be understood that the embodiments above are non-limiting and other applications, harmonic generation-based triggering system configurations, and harmonic generation-based triggering methods are possible. The systems and methods of the present invention are not limited to any particular number of components, type of components (e.g., type of harmonic generation material, photosensitive material, agent, electromagnetic source), and/or target environment. Moreover, one or more harmonic generation-based triggering systems and/or methods may be utilized in a given application.

The following examples are intended to illustrate certain embodiments of the present invention, but do not exemplify the full scope of the invention.

Example 1

This example describes using collagen as a harmonic generation material to cleave a bond and uncage a caged fluorescein molecule attached to the collagen surface. This example illustrates that collagen can convert near infrared (NIR) electromagnetic radiation to ultraviolet electromagnetic radiation, which can be used to cleave a photosensitive linker, resulting in the uncaging of a molecule bound to the surface of the collagen by the photosensitive linker.

Figure 5:
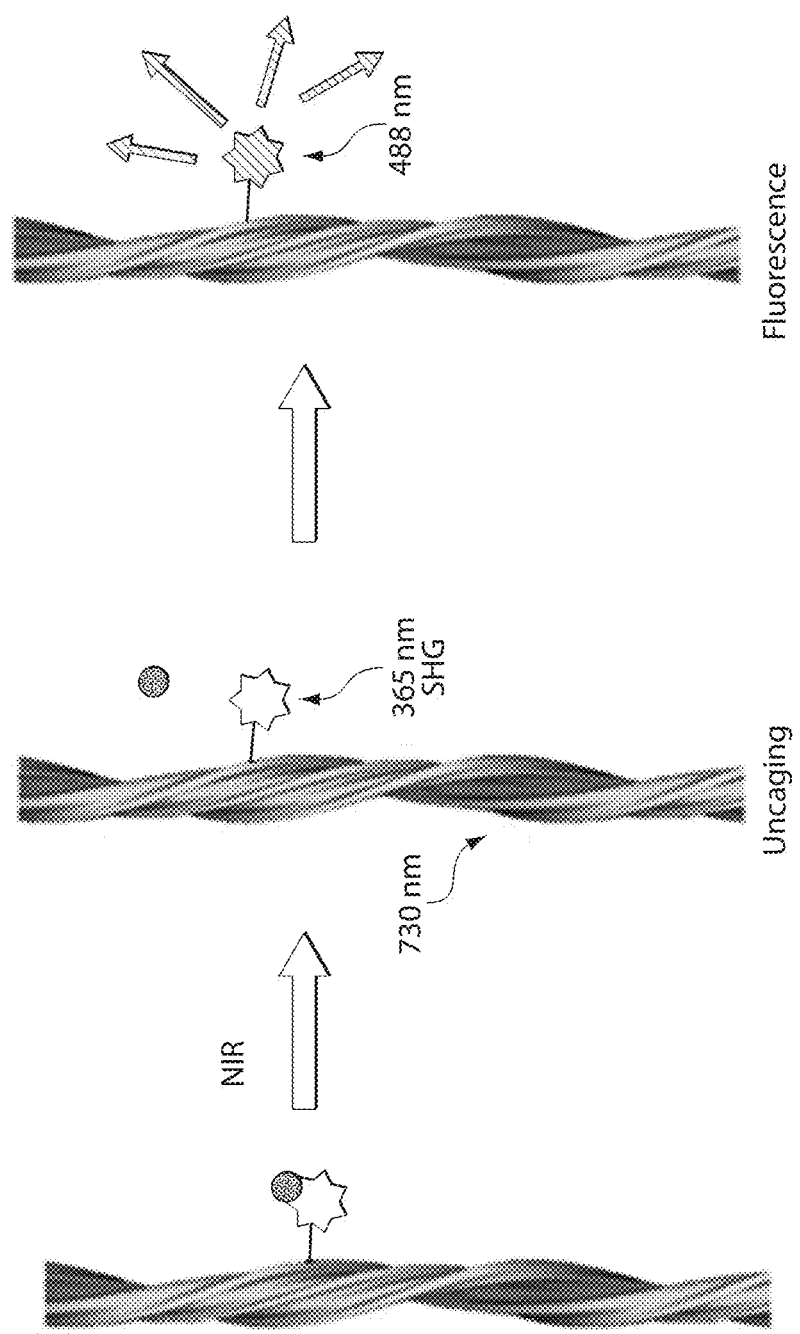
FIG. 5 is, in accordance with one set of embodiments, a schematic illustration of a triggering system in which collagen is used as a harmonic generation material and caged fluorescein is used as a photosensitive material.
Figure 6:
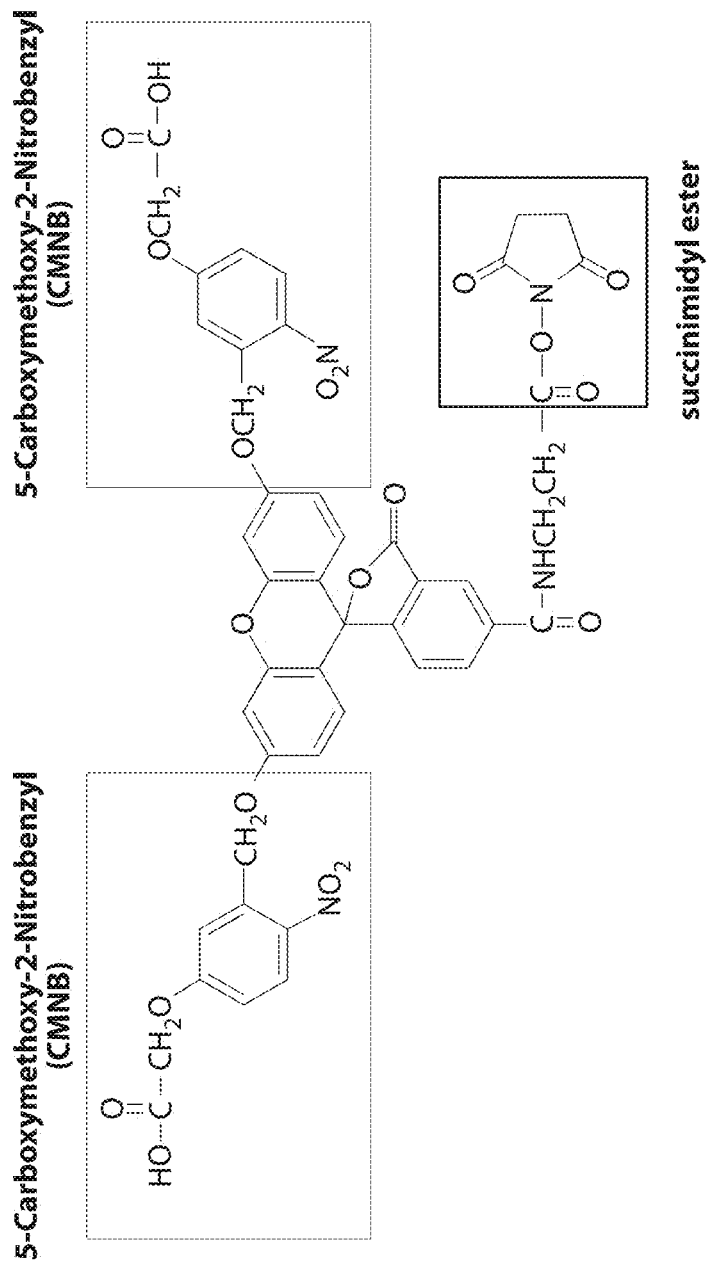
FIG. 6 is a schematic illustration of a caged fluorescein molecule, according to certain embodiments.

FIG. 5 is a schematic illustration of the arrangement of the collagen and caged fluorescein employed in this example. Referring to FIG. 6, a caged fluorescein molecule including an N-hydroxysuccinimide group (to allow binding to the amine group of the collagen) and two 5-carboxymethoxy-2-nitrobenzyl (CMNB) caging groups was employed. Referring back to FIG. 5, the collagen (to which the caged fluorescein was attached) was irradiated using near infrared radiation having a wavelength of 730 nm and at an intensity of 3 Wcm$^{-2}$. Upon irradiation of the collagen, ultraviolet electromagnetic radiation having a wavelength of 365 nm was generated. The ultraviolet electromagnetic radiation was absorbed by the caged fluorescein, resulting in the cleavage of the caging groups and the uncaging of the fluorescein.

Figure 7A:
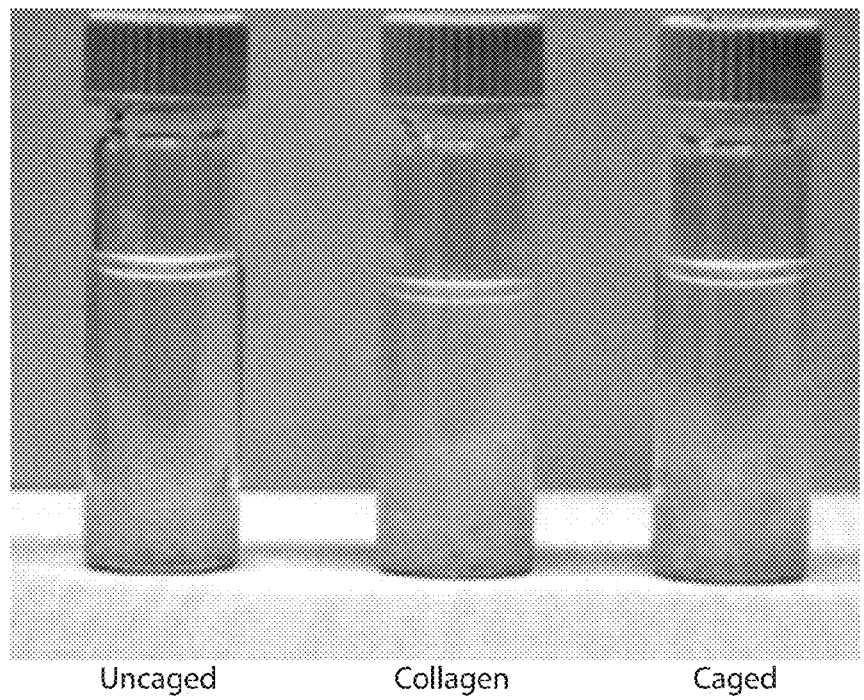
FIGS. 7A-7B are photographs of caged fluorescein bound to collagen, uncaged fluorescein bound to collagen, and unmodified collagen, according to some embodiments.
Figure 7B:
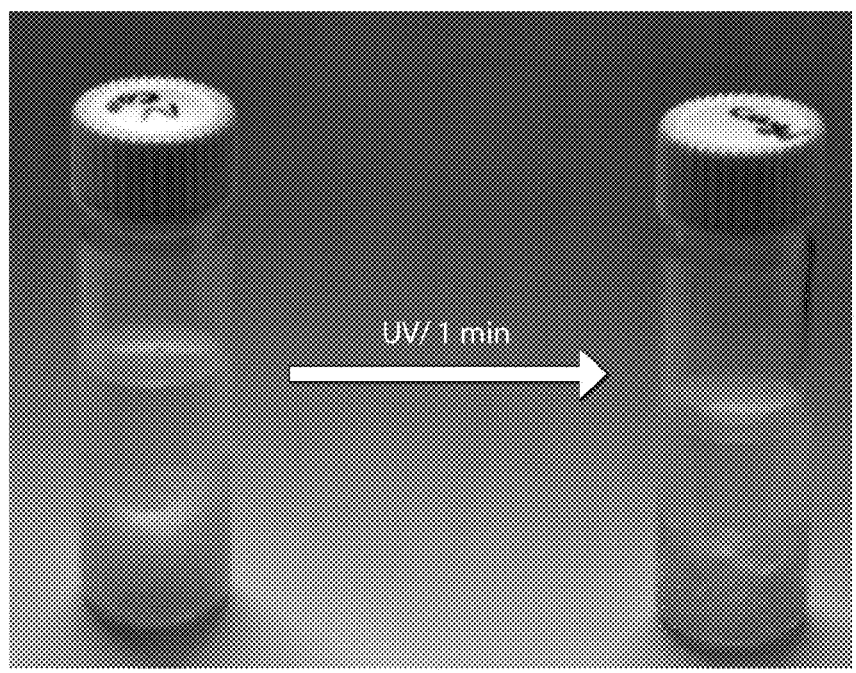

FIGS. 7A-7B are photographs showing caged and uncaged fluorescein bound to collagen, as well as pristine collagen. The caged fluorescein exhibited no color. However, upon irradiating the collagen fluorescein couple with ultraviolet electromagnetic radiation, After confirming that exposure to ultraviolet electromagnetic radiation produces uncaging of the fluorescein, a second set of experiments was performed in which the collagen/caged fluorescein complex was exposed to near infrared electromagnetic radiation. In this set of experiments, the uncaging of the fluorescein was detected using a fluorescent microscope. The collagen/caged fluorescein complex was exposed to near infrared electromagnetic radiation (having a wavelength of 730 nm) from a continuous wave laser for a period of 30 minutes and at an intensity of 3 Wcm$^{-2}$.

Figure 8:
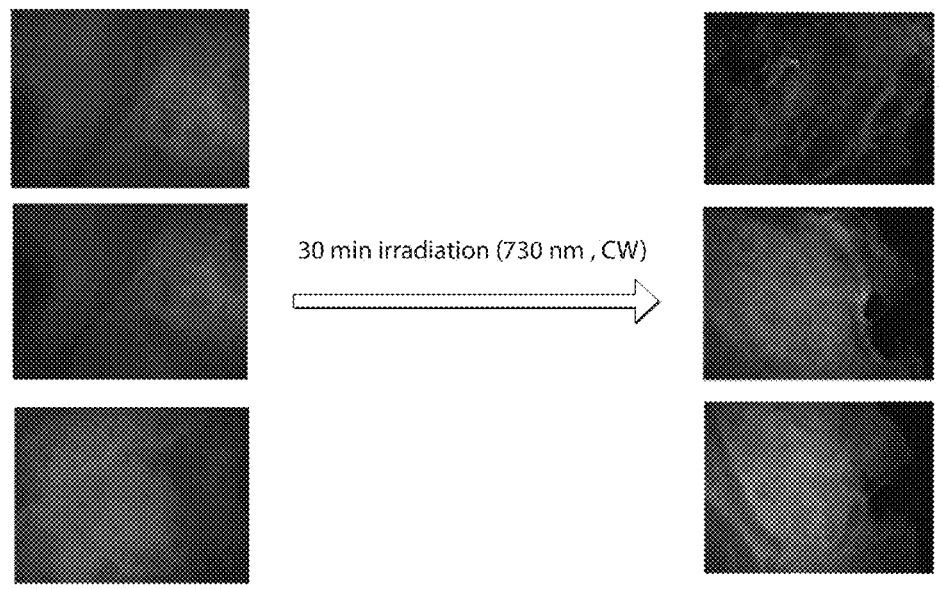
FIG. 8 are fluorescent microscope images showing the response of a collagen/fluorescein complex to incident infrared electromagnetic radiation, before and after uncaging of the fluorescein, according to one set of embodiments.

As shown in FIG. 8, upon exposure of the complex to the near infrared radiation, an increase in fluorescent intensity was detected due to the uncaging of the fluorescein. A green color was observed, indicating that the emitted light was generated by the florescence of the uncaged group, and did not correspond to the ultraviolet light generated by the collagen. The collagen-generated ultraviolet light which was subsequently absorbed by the caged fluorescein. Subsequently, the caged fluorescein was uncaged due to the absorption of ultraviolet light.

Comparative Example 1

Figure 9:
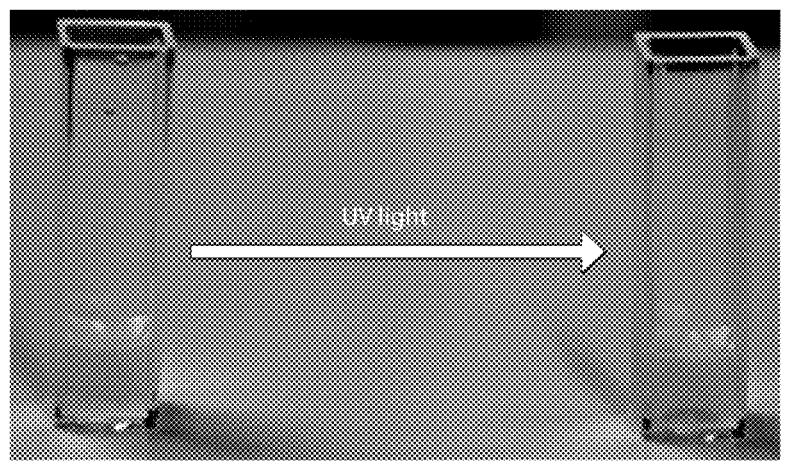
FIG. 9 is an exemplary photograph of a first silica/caged fluorescein sample that is not irradiated with ultraviolet electromagnetic radiation and a second silica/caged fluorescein sample that is irradiated with ultraviolet electromagnetic radiation.
Figure 10:
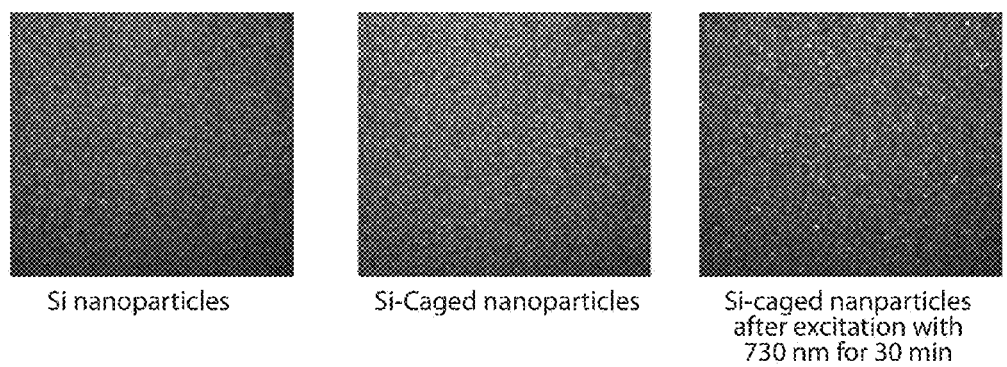
FIG. 10 is an exemplary series of fluorescent microscope images illustrating the effect of exposing a silica/caged fluorescein complex to infrared electromagnetic radiation.

This example describes the control experiment for Example 1. The procedure for the control experiment was identical to Example 1, except the caged fluorescein illustrated in FIG. 6 was bound to silica nanoparticles, which are not second harmonic generation materials, instead of collagen. Using similar procedures to those described in Example 1, the silica/caged-fluorescein complex was irradiated with ultraviolet electromagnetic radiation. Direct irradiation of the complex with ultraviolet light uncaged the fluorescein molecules, causing a very clear color change as shown in FIG. 9. However, when the silica/caged-fluorescein complex was irradiated with near infrared electromagnetic radiation (with the same laser power and for the same amount of time described in Example 1), no increase in fluorescent intensity was observed, as shown in FIG. 10.

Example 2

This example describes the cleavage of a photocleavable bond in a molecule directly bound to the collagen.

Figure 11:
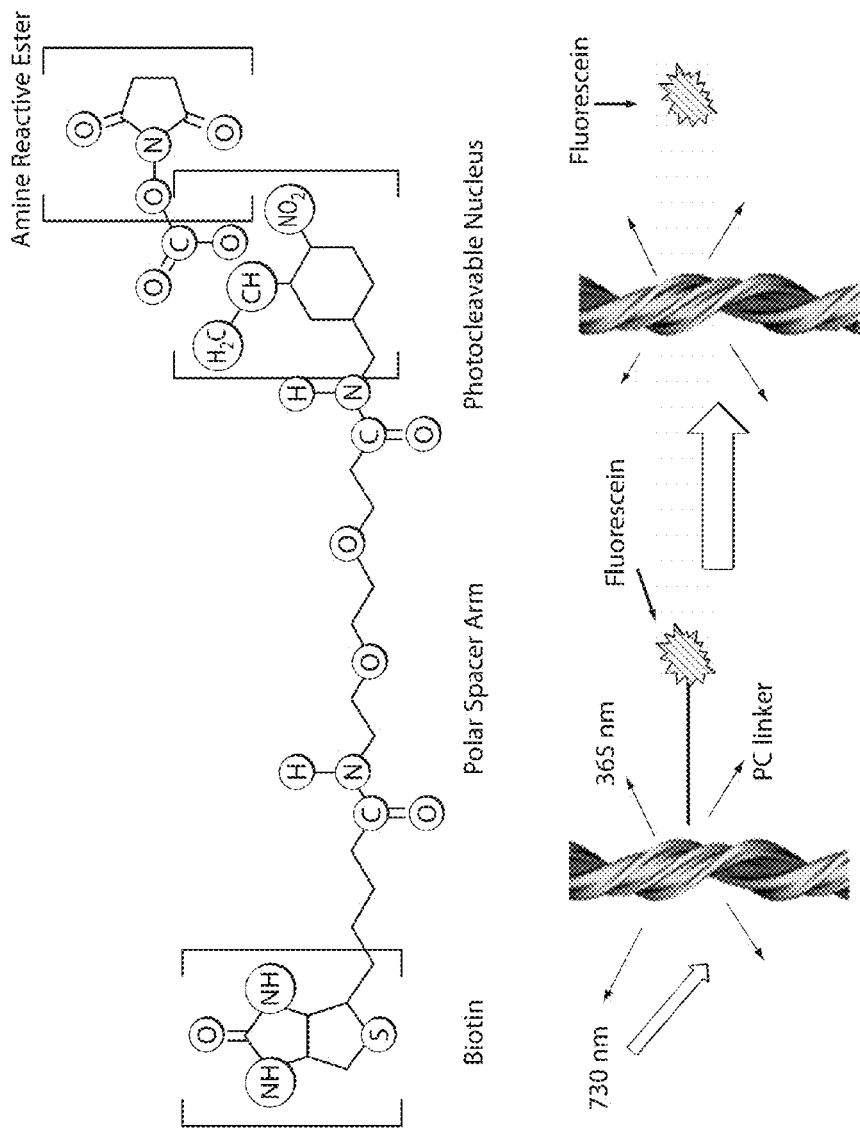
FIG. 11 is, according to certain embodiments, a schematic illustration of a triggering system in which collagen is used as a harmonic generation material to emit electromagnetic radiation that cleaves a photocleavable linker molecule.
Figure 12:
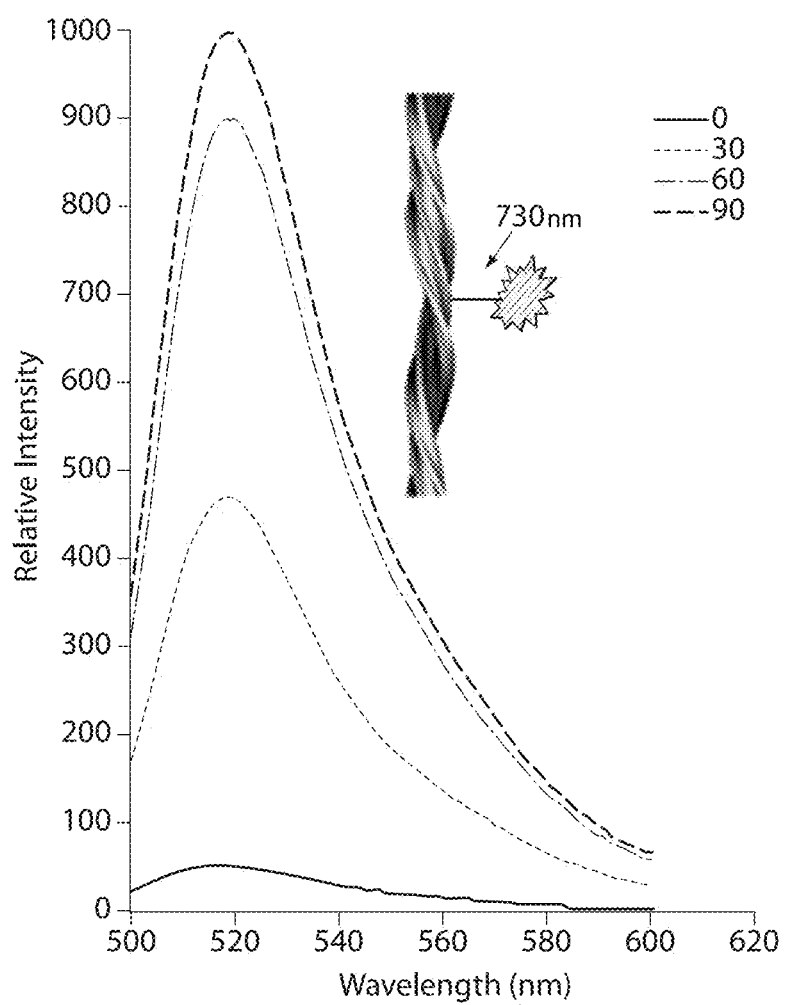
FIG. 12 is an exemplary plot of fluorescent intensity as a function of emitted wavelength in a system in which a photosensitive linker molecule binds fluorescein to collagen, according to some embodiments.

FIG. 11 is a schematic illustration of the reaction employed in this example. Fluorescein was attached to collagen using a photocleavable (PC) linker. The PC linker had an N-hydroxysuccinimide group on one end that was bound to the collagen and a biotin on the other end that was bound to a streptavidin fluorescein. The PC linker was cleavable at 365 nm. In a reaction solution, the efficiency of the binding was assessed via an increase in the fluorescent intensity on the reaction solution due to the cleavage of the streptavidin fluorescein. In this reaction, a collagen solution (in buffer) was irradiated with near infrared light (using a continuous wave laser emitting 730 nm radiation at an intensity of 3 Wcm$^{-2}$) or UV light. Supernatant aliquots were taken and their fluorescent intensity was measured. FIG. 12 is a plot of fluorescent intensity as a function of emitted wavelength, for irradiation times of 0, 30, 60, and 90 minutes. As illustrated in FIG. 12, irradiation of the collagen with near infrared electromagnetic radiation resulted in an increase in fluorescent intensity, indicating that the PC linker between the fluorescein and the collagen had been cleaved.

Comparative Example 2

Figure 13A:
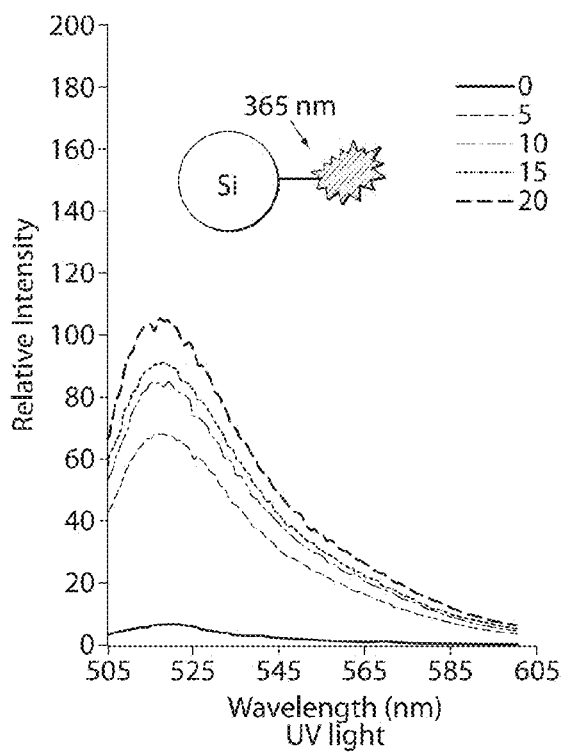
FIGS. 13A-13B are exemplary plots of fluorescent intensity as a function of emitted wavelength—upon exposure to ultraviolet and infrared electromagnetic radiation, respectively—in a system in which a photosensitive linker molecule binds fluorescein to silica.
Figure 13B:
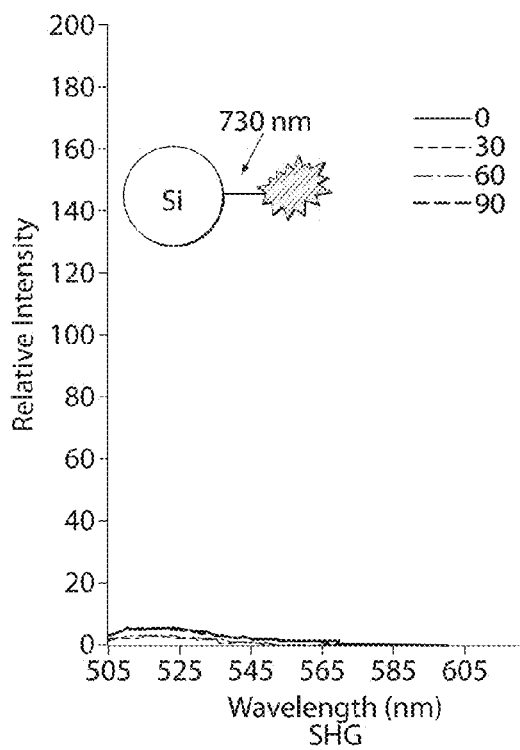

This example describes the control experiment for Example 2. The procedure for the control experiment was identical to Example 2, except the fluorescein was bound to silica nanoparticles, which are not second harmonic generation materials, instead of collagen. Using similar procedures to those described in Example 2, the silica/fluorescein complex was irradiated with ultraviolet electromagnetic radiation. Direct irradiation of the complex with ultraviolet light cleaved the photosensitive linker, causing a large increase in fluorescent intensity, as shown in FIG. 13A. However, when the silica/fluorescein complex was irradiated with near infrared electromagnetic radiation (with the same laser power described in Example 2), no increase in fluorescent intensity was observed, as shown in FIG. 13B.

Example 3

This example describes a harmonic generation-based triggering system in a bodily tissue.

Figure 14:
FIG. 14 is an exemplary schematic diagram illustrating a system in which caged fluorescein is bound to a cornea, according to one set of embodiments.
Figure 15:
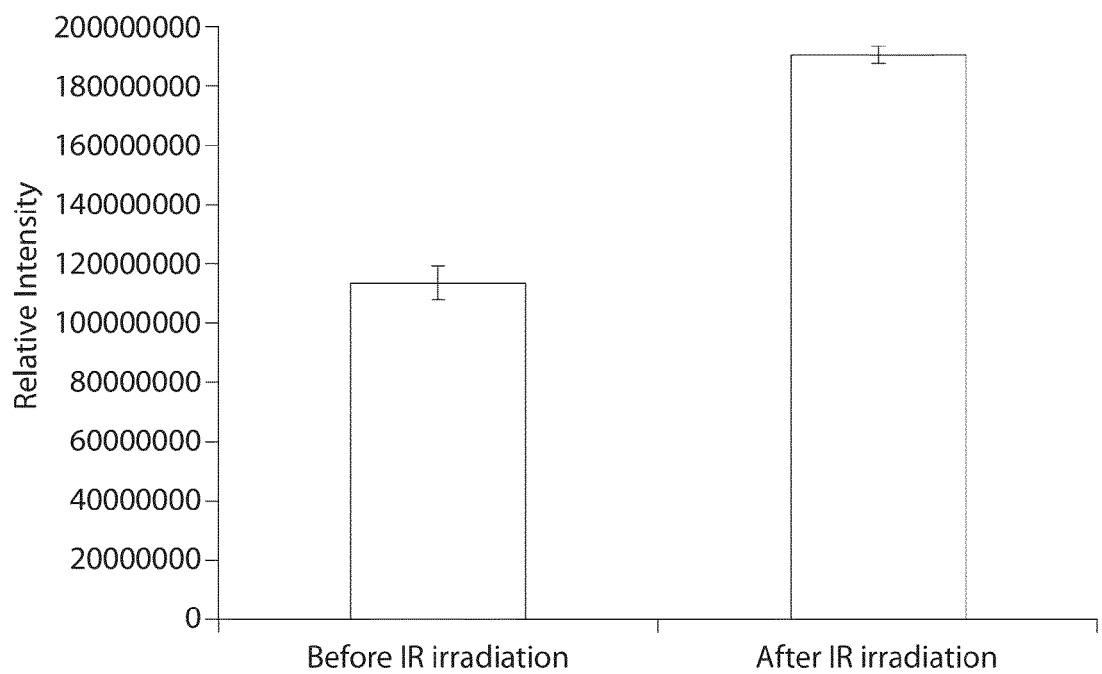
FIG. 15 is an exemplary plot of fluorescent intensity before and after illumination of the system illustrated in FIG. 14 with infrared electromagnetic radiation, according to certain embodiments.

An ex vivo experiment was conducted using pigs' corneas. The caged fluorescein, as described in Example 1, was reacted with the corneas. After overnight incubation, fluorescent images were taken. A schematic illustration of the reaction design is shown in FIG. 14. To assess the change in fluorescent intensity, fluorescent microscope images were treated with ImageJ and converted into total intensity. FIG. 15 shows the significant increase of fluorescent intensity after near infrared (NIR) irradiation. The collagen in the cornea efficiently converted NIR light into ultraviolet light, and uncaged a fluorescein molecule tethered to the surface of the cornea.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
exposing, to a harmonic generation material, electromagnetic radiation of a first frequency such that the harmonic generation material converts at least a portion of the electromagnetic radiation of the first frequency to electromagnetic radiation of a second, higher frequency, and the harmonic generation material releases the electromagnetic radiation of the second, higher frequency;
wherein:
the electromagnetic radiation of the second frequency is exposed to a material photosensitive to the electromagnetic radiation of the second frequency such that when the photosensitive material absorbs the electromagnetic radiation of the second frequency, the photosensitive material is physically and/or chemically altered;
the closest distance between the harmonic generation material and the photosensitive material is less than about 1 centimeter; and
the electromagnetic radiation of the first frequency has a wavelength less than or equal to about 2500 nm.

2. The method of claim 1, wherein exposing the electromagnetic radiation of the first frequency to the harmonic generation material comprises exposing at least one frequency of infrared electromagnetic radiation to the harmonic generation material.

3. The method of claim 1, wherein exposing the electromagnetic radiation of the first frequency to the harmonic generation material comprises directing a source of the electromagnetic radiation toward the harmonic generation material.

4. The method of claim 1, wherein, when the photosensitive material absorbs the electromagnetic radiation of the second frequency, at least one chemical bond of the photosensitive material is broken.

5. The method of claim 4, wherein, when the at least one chemical bond of the photosensitive material is broken, the photosensitive material is cleaved into a first portion and a second, separate portion.

6. The method of claim 5, wherein the second, separate portion of the photosensitive material is bound to an agent, and breaking the chemical bond leads to delivery of the agent.

7. The method of claim 4, wherein, when the at least one chemical bond of the photosensitive material is broken, a transport passageway is opened within the photosensitive material.

8. The method of claim 7, wherein the photosensitive material at least partially surrounds an agent, and opening the transport passageway within the photosensitive material results in delivery of the agent.

9. The method of claim 1, wherein, when the photosensitive material absorbs the electromagnetic radiation of the second frequency, the molecular conformation of the photosensitive material is altered.

10. The method of claim 9, wherein altering the conformation of the photosensitive material causes an agent associated with the photosensitive material to be released to a target environment.

11. The method of claim 10, wherein altering the conformation of the photosensitive material causes an agent associated with the photosensitive material to be activated.

12. The method of claim 1, wherein the photosensitive material is part of a particle.

13. The method of claim 1, wherein the release of the electromagnetic radiation of a second, higher frequency is part of a second-harmonic generation process.

14. The method of claim 1, wherein the harmonic generation material comprises collagen and/or myosin.

15. The method of claim 14, wherein the harmonic generation material comprises collagen and/or myosin that is part of a bodily tissue of a subject.

16. The method of claim 1, wherein the harmonic generation material comprises at least one of $LiNbO_3$, $BaTiO_3$, $KTiO_3$, $KTiOPO_4$, $LiB_3O_5$, ammonium dihydrogen phosphate, $KH_2PO_4$, MgO, $KNbO_3$, $\beta$-$BaB_2O_4$, and $LiIO_3$.

17. The method of claim 2, wherein exposing the harmonic generation material to a first frequency of infrared electromagnetic radiation results in the harmonic generation material releasing a second frequency of ultraviolet electromagnetic radiation.

18. The method of claim 1, wherein the photosensitive material comprises azobenzene, o-nitrobenzyl, coumarin, a phenacyl group, a benzoin ester, a desyl compound, an arylazidoalcohol, nitroveratryloxycarbonyl (NVOC), 2-(dimethylamino)-5-nitrophenyl (DANP), Bis(o-nitrophenyl) ethanediol, brominated hydroxyquinoline, a dinitrobenzenesulfenyl ester, a nitroindoline, an o-nitrophenylene glycol, a dithiane, a bezyl alcohol, a sulphonamide, a polycyclic aromatic hydrocarbon, and/or a carbamate.

19. The method of claim 1, wherein the harmonic generation converts the electromagnetic radiation of the first frequency to electromagnetic radiation of the second, higher frequency at an efficiency of at least about $10^{-10}$ when illuminated with electromagnetic radiation of the first frequency at an intensity of $10^{11}$ W/cm$^2$.

20. The method of claim 3, wherein directing the source of electromagnetic radiation of the first frequency toward the harmonic generation material comprises irradiating bodily tissue with the electromagnetic radiation of the first frequency.

* * * * *